United States Patent
Yang et al.

(10) Patent No.: US 12,365,730 B2
(45) Date of Patent: Jul. 22, 2025

(54) ANTI-CD79B ANTIBODY, ANTIGEN-BINDING FRAGMENT THEREOF, AND PHARMACEUTICAL USE THEREOF

(71) Applicant: Tuojie Biotech (Shanghai) Co., Ltd., Shanghai (CN)

(72) Inventors: Cuiqing Yang, Shanghai (CN); Renhong Tang, Shanghai (CN)

(73) Assignee: Tuojie Biotech (Shanghai) Co., Ltd., Shanghai (CN)

( * ) Notice: Subject to any disclaimer, the term of this patent is extended or adjusted under 35 U.S.C. 154(b) by 870 days.

(21) Appl. No.: 17/310,204

(22) PCT Filed: Jan. 22, 2020

(86) PCT No.: PCT/CN2020/073803
§ 371 (c)(1),
(2) Date: Jul. 26, 2021

(87) PCT Pub. No.: WO2020/156439
PCT Pub. Date: Aug. 6, 2020

(65) Prior Publication Data
US 2022/0162304 A1    May 26, 2022

(30) Foreign Application Priority Data

Jan. 28, 2019 (CN) .......................... 201910083330.4

(51) Int. Cl.
| | | |
|---|---|---|
| *C07K 16/28* | (2006.01) | |
| *A61K 39/00* | (2006.01) | |
| *A61P 35/00* | (2006.01) | |

(52) U.S. Cl.
CPC .......... *C07K 16/2803* (2013.01); *A61P 35/00* (2018.01); *A61K 2039/505* (2013.01); *C07K 2317/24* (2013.01); *C07K 2317/33* (2013.01); *C07K 2317/73* (2013.01); *C07K 2317/77* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | |
|---|---|---|
| 9,085,630 B2 | 7/2015 | Crowley et al. |
| 2009/0028856 A1 | 1/2009 | Chen et al. |
| 2016/0376371 A1* | 12/2016 | Ravetch .............. A61P 35/00 424/133.1 |
| 2017/0226207 A1 | 8/2017 | Yamajuku et al. |
| 2017/0362318 A1 | 12/2017 | Crowley et al. |

FOREIGN PATENT DOCUMENTS

| | | |
|---|---|---|
| CN | 101802013 A | 8/2010 |
| CN | 101981055 A | 2/2011 |
| WO | 03048731 A2 | 6/2003 |
| WO | 2009012256 A1 | 1/2009 |
| WO | 2009012268 A1 | 1/2009 |
| WO | 2009099728 A1 | 8/2009 |
| WO | 2014011519 A1 | 1/2014 |
| WO | 2014011521 A1 | 1/2014 |
| WO | 2014177615 A2 | 11/2014 |
| WO | 2016040856 A2 | 3/2016 |
| WO | 2016090210 A1 | 6/2016 |
| WO | 2016205176 A1 | 12/2016 |
| WO | 2017009474 A1 | 1/2017 |
| WO | 2016021621 A1 | 6/2017 |

OTHER PUBLICATIONS

Mallbris et al. Molecular Insights into Fully Human and Humanized Monoclonal Antibodies. 2016. J Clinic Aesth Dermatol. 9(7): 13-15. (Year: 2016).*
Umar et al. Future directions in cancer prevention. 2012. Nat Rev. 12:835-848. (Year: 2012).*
Bode and Dong. Cancer prevention research—then and now. 2009. Nat Rev. 9:508-516. (Year: 2009).*
Sarfati and Gurney. Preventing cancer: the only way forward. 2022. Lancet 400:540-541. (Year: 2022).*
Kaczmarek et al. Cancer Vaccine Therapeutics: Limitations and Effectiveness—A Literature Review. 2023. Cells 12:2159: 1-27. (Year: 2023).*
Zheng et al. In vivo effects of targeting CD79b with antibodies and antibody-drug conjugates. 2009. Mol Cancer Ther 8(10):2937-2946. (Year: 2009).*

(Continued)

*Primary Examiner* — Daniel E Kolker
*Assistant Examiner* — Maureen Varina Driscoll
(74) *Attorney, Agent, or Firm* — Taft Stettinius & Hollister LLP

(57) ABSTRACT

The present invention relates to an anti-CD79B antibody, an antigen-binding fragment thereof, and a pharmaceutical use thereof. Furthermore, the present invention relates to a chimeric antibody and a humanized antibody comprising a CDR region of the anti-CD79B antibody, a pharmaceutical composition comprising the anti-CD79B antibody or the antigen-binding fragment thereof, and a use thereof as an anti-cancer drug. Particularly, the present invention relates to a humanized anti-CD79B antibody, and a use thereof in preparation of a drug for treating lymphoma (such as DLBCL).

22 Claims, 5 Drawing Sheets

Specification includes a Sequence Listing.

(56) References Cited

OTHER PUBLICATIONS

Written Opinion of the International Searching Authority; China National Intellectual Property Administration; International Application No. PCT/CN2020/073803; Apr. 27, 2020; 6 pages.

International Preliminary Report on Patentability; The International Bureau of WIPO; International Application No. PCT/CN2020/073803; Jul. 27, 2021; 7 pages.

International Search Report; China National Intellectual Property Administration; International Application No. PCT/CN2020/073803; Apr. 27, 2020; 9 pages.

\* cited by examiner

SEQUENCE LISTING

```
<160> NUMBER OF SEQ ID NOS: 26

<210> SEQ ID NO 1
<211> LENGTH: 433
<212> TYPE: PRT
<213> ORGANISM: Artificial Sequence
<220> FEATURE:
<221> NAME/KEY: PEPTIDE
<222> LOCATION: (0)..(433)
<223> OTHER INFORMATION: Human CD79B ECD-hFc

<400> SEQUENCE: 1

Ala Arg Ser Glu Asp Arg Tyr Arg Asn Pro Lys Gly Ser Ala Cys Ser
1               5                   10                  15

Arg Ile Trp Gln Ser Pro Arg Phe Ile Ala Arg Lys Arg Gly Phe Thr
            20                  25                  30

Val Lys Met His Cys Tyr Met Asn Ser Ala Ser Gly Asn Val Ser Trp
        35                  40                  45

Leu Trp Lys Gln Glu Met Asp Glu Asn Pro Gln Gln Leu Lys Leu Glu
    50                  55                  60

Lys Gly Arg Met Glu Glu Ser Gln Asn Glu Ser Leu Ala Thr Leu Thr
```

```
                65                  70                  75                  80
        Ile Gln Gly Ile Arg Phe Glu Asp Asn Gly Ile Tyr Phe Cys Gln Gln
                        85                  90                  95

Lys Cys Asn Asn Thr Ser Glu Val Tyr Gln Gly Cys Gly Thr Glu Leu
                        100                 105                 110

Arg Val Met Gly Phe Ser Thr Leu Ala Gln Leu Lys Gln Arg Asn Thr
                        115                 120                 125

Leu Lys Asp Gly Ile Ile Met Ile Gln Thr Leu Leu Ile Ile Leu Phe
                        130                 135                 140

Ile Ile Val Pro Ile Phe Leu Leu Leu Asp Lys Asp Asp Ser Lys Ala
        145                 150                 155                 160

Gly Met Glu Glu Asp His Thr Tyr Glu Gly Leu Asp Ile Asp Gln Thr
                        165                 170                 175

Ala Thr Tyr Glu Asp Ile Val Thr Leu Arg Thr Gly Glu Val Lys Trp
                        180                 185                 190

Ser Val Gly Glu His Pro Gly Gln Glu Glu Pro Lys Ser Cys Asp Lys
                        195                 200                 205

Thr His Thr Cys Pro Pro Cys Pro Ala Pro Glu Leu Leu Gly Gly Pro
        210                 215                 220

Ser Val Phe Leu Phe Pro Pro Lys Pro Lys Asp Thr Leu Met Ile Ser
        225                 230                 235                 240

Arg Thr Pro Glu Val Thr Cys Val Val Val Asp Val Ser His Glu Asp
                        245                 250                 255

Pro Glu Val Lys Phe Asn Trp Tyr Val Asp Gly Val Glu Val His Asn
                        260                 265                 270

Ala Lys Thr Lys Pro Arg Glu Glu Gln Tyr Asn Ser Thr Tyr Arg Val
                        275                 280                 285

Val Ser Val Leu Thr Val Leu His Gln Asp Trp Leu Asn Gly Lys Glu
                        290                 295                 300

Tyr Lys Cys Lys Val Ser Asn Lys Ala Leu Pro Ala Pro Ile Glu Lys
        305                 310                 315                 320

Thr Ile Ser Lys Ala Lys Gly Gln Pro Arg Glu Pro Gln Val Tyr Thr
                        325                 330                 335

Leu Pro Pro Ser Arg Glu Glu Met Thr Lys Asn Gln Val Ser Leu Thr
                        340                 345                 350

Cys Leu Val Lys Gly Phe Tyr Pro Ser Asp Ile Ala Val Glu Trp Glu
                        355                 360                 365

Ser Asn Gly Gln Pro Glu Asn Asn Tyr Lys Thr Thr Pro Pro Val Leu
                        370                 375                 380

Asp Ser Asp Gly Ser Phe Phe Leu Tyr Ser Lys Leu Thr Val Asp Lys
        385                 390                 395                 400

Ser Arg Trp Gln Gln Gly Asn Val Phe Ser Cys Ser Val Met His Glu
                        405                 410                 415

Ala Leu His Asn His Tyr Thr Gln Lys Ser Leu Ser Leu Ser Pro Gly
                        420                 425                 430

Lys

<210> SEQ ID NO 2
<211> LENGTH: 207
<212> TYPE: PRT
<213> ORGANISM: Artificial Sequence
<220> FEATURE:
<221> NAME/KEY: PEPTIDE
<222> LOCATION: (0)..(207)
<223> OTHER INFORMATION: Human CD79B ECD-His
```

<400> SEQUENCE: 2

```
Ala Arg Ser Glu Asp Arg Tyr Arg Asn Pro Lys Gly Ser Ala Cys Ser
1               5                   10                  15

Arg Ile Trp Gln Ser Pro Arg Phe Ile Ala Arg Lys Arg Gly Phe Thr
            20                  25                  30

Val Lys Met His Cys Tyr Met Asn Ser Ala Ser Gly Asn Val Ser Trp
        35                  40                  45

Leu Trp Lys Gln Glu Met Asp Glu Asn Pro Gln Gln Leu Lys Leu Glu
50                  55                  60

Lys Gly Arg Met Glu Glu Ser Gln Asn Glu Ser Leu Ala Thr Leu Thr
65                  70                  75                  80

Ile Gln Gly Ile Arg Phe Glu Asp Asn Gly Ile Tyr Phe Cys Gln Gln
                85                  90                  95

Lys Cys Asn Asn Thr Ser Glu Val Tyr Gln Gly Cys Gly Thr Glu Leu
            100                 105                 110

Arg Val Met Gly Phe Ser Thr Leu Ala Gln Leu Lys Gln Arg Asn Thr
        115                 120                 125

Leu Lys Asp Gly Ile Ile Met Ile Gln Thr Leu Leu Ile Ile Leu Phe
130                 135                 140

Ile Ile Val Pro Ile Phe Leu Leu Leu Asp Lys Asp Ser Lys Ala
145                 150                 155                 160

Gly Met Glu Glu Asp His Thr Tyr Glu Gly Leu Asp Ile Asp Gln Thr
                165                 170                 175

Ala Thr Tyr Glu Asp Ile Val Thr Leu Arg Thr Gly Glu Val Lys Trp
            180                 185                 190

Ser Val Gly Glu His Pro Gly Gln Glu His His His His His His
        195                 200                 205
```

<210> SEQ ID NO 3
<211> LENGTH: 117
<212> TYPE: PRT
<213> ORGANISM: Artificial Sequence
<220> FEATURE:
<221> NAME/KEY: CHAIN
<222> LOCATION: (0)..(117)
<223> OTHER INFORMATION: Mouse hybridoma monoclonal antibody mAb015
      heavy chain variable region

<400> SEQUENCE: 3

```
Gln Val Gln Leu Gln Gln Ser Gly Ala Glu Leu Ala Arg Pro Gly Ala
1               5                   10                  15

Ser Val Lys Leu Ser Cys Lys Ala Ser Gly Ser Ser Phe Thr Ser Tyr
            20                  25                  30

Gly Ile Asn Trp Val Lys Gln Arg Thr Gly Gln Gly Leu Glu Trp Ile
        35                  40                  45

Gly Glu Ile Phe Pro Arg Ser Gly Asn Thr Tyr Tyr Asn Glu Lys Phe
50                  55                  60

Glu Gly Lys Ala Thr Leu Thr Ala Asp Lys Ser Ser Ser Thr Ala Tyr
65                  70                  75                  80

Met Glu Leu Arg Ser Leu Thr Ser Glu Asp Ser Ala Val Tyr Phe Cys
                85                  90                  95

Ala Lys Gly Asp Leu Gly Asp Phe Asp Tyr Trp Gly Gln Gly Thr Thr
            100                 105                 110

Leu Thr Val Ser Ser
        115
```

```
<210> SEQ ID NO 4
<211> LENGTH: 112
<212> TYPE: PRT
<213> ORGANISM: Artificial Sequence
<220> FEATURE:
<221> NAME/KEY: CHAIN
<222> LOCATION: (0)..(112)
<223> OTHER INFORMATION: Mouse hybridoma monoclonal antibody mAb015
      light chain variable region

<400> SEQUENCE: 4

Asp Phe Leu Met Thr Gln Thr Pro Leu Ser Leu Pro Val Arg Leu Gly
1               5                   10                  15

Asp Gln Ala Ser Ile Ser Cys Arg Ser Ser Gln Ser Ile Val His Ser
            20                  25                  30

Asp Gly Asn Thr Tyr Phe Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Trp Thr Phe Gly Gly Gly Thr Lys Leu Glu Ile Lys
            100                 105                 110

<210> SEQ ID NO 5
<211> LENGTH: 119
<212> TYPE: PRT
<213> ORGANISM: Artificial Sequence
<220> FEATURE:
<221> NAME/KEY: CHAIN
<222> LOCATION: (0)..(119)
<223> OTHER INFORMATION: Mouse hybridoma monoclonal antibody mAb017
      heavy chain variable region

<400> SEQUENCE: 5

Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Phe Thr Thr Tyr
            20                  25                  30

Gly Ile Asn Trp Val Lys Gln Arg Thr Gly Gln Gly Leu Glu Trp Ile
        35                  40                  45

Gly Glu Ile Tyr Pro Arg Ser Gly Asn Ile Tyr Tyr Asn Glu Lys Phe
    50                  55                  60

Lys Gly Lys Ala Thr Leu Thr Ala Asp Lys Ser Ser Ser Thr Ala Tyr
65                  70                  75                  80

Met Glu Leu Arg Ser Leu Thr Ser Glu Asp Ser Ala Val Tyr Phe Cys
                85                  90                  95

Ala Arg Gly Ser Asp Tyr Asp Gly Asp Phe Ala Tyr Trp Gly Gln Gly
            100                 105                 110

Thr Leu Val Thr Val Ser Ala
        115

<210> SEQ ID NO 6
<211> LENGTH: 112
<212> TYPE: PRT
<213> ORGANISM: Artificial Sequence
<220> FEATURE:
<221> NAME/KEY: CHAIN
<222> LOCATION: (0)..(112)
```

<223> OTHER INFORMATION: Mouse hybridoma monoclonal antibody mAb017
    light chain variable region

<400> SEQUENCE: 6

```
Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His
            20                  25                  30

Asp Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Trp Thr Phe Gly Gly Gly Thr Gln Leu Glu Ile Lys
            100                 105                 110
```

<210> SEQ ID NO 7
<211> LENGTH: 7
<212> TYPE: PRT
<213> ORGANISM: Artificial Sequence
<220> FEATURE:
<221> NAME/KEY: DOMAIN
<222> LOCATION: (0)..(7)
<223> OTHER INFORMATION: mAb015 heavy chain CDR1

<400> SEQUENCE: 7

```
Gly Ser Ser Phe Thr Ser Tyr
1               5
```

<210> SEQ ID NO 8
<211> LENGTH: 6
<212> TYPE: PRT
<213> ORGANISM: Artificial Sequence
<220> FEATURE:
<221> NAME/KEY: DOMAIN
<222> LOCATION: (0)..(6)
<223> OTHER INFORMATION: mAb015 heavy chain CDR2

<400> SEQUENCE: 8

```
Phe Pro Arg Ser Gly Asn
1               5
```

<210> SEQ ID NO 9
<211> LENGTH: 8
<212> TYPE: PRT
<213> ORGANISM: Artificial Sequence
<220> FEATURE:
<221> NAME/KEY: DOMAIN
<222> LOCATION: (0)..(8)
<223> OTHER INFORMATION: mAb015 heavy chain CDR3

<400> SEQUENCE: 9

```
Gly Asp Leu Gly Asp Phe Asp Tyr
1               5
```

<210> SEQ ID NO 10
<211> LENGTH: 16
<212> TYPE: PRT
<213> ORGANISM: Artificial Sequence
<220> FEATURE:
<221> NAME/KEY: DOMAIN
<222> LOCATION: (0)..(16)

<223> OTHER INFORMATION: mAb015 light chain CDR1

<400> SEQUENCE: 10

Arg Ser Ser Gln Ser Ile Val His Ser Asp Gly Asn Thr Tyr Phe Glu
1               5                   10                  15

<210> SEQ ID NO 11
<211> LENGTH: 7
<212> TYPE: PRT
<213> ORGANISM: Artificial Sequence
<220> FEATURE:
<221> NAME/KEY: DOMAIN
<222> LOCATION: (0)..(7)
<223> OTHER INFORMATION: mAb015 mAb016 mAb017 light chain CDR2

<400> SEQUENCE: 11

Lys Val Ser Asn Arg Phe Ser
1               5

<210> SEQ ID NO 12
<211> LENGTH: 9
<212> TYPE: PRT
<213> ORGANISM: Artificial Sequence
<220> FEATURE:
<221> NAME/KEY: DOMAIN
<222> LOCATION: (0)..(9)
<223> OTHER INFORMATION: mAb015 mAb016 mAb017 light chain CDR3

<400> SEQUENCE: 12

Phe Gln Gly Ser His Val Pro Trp Thr
1               5

<210> SEQ ID NO 13
<211> LENGTH: 7
<212> TYPE: PRT
<213> ORGANISM: Artificial Sequence
<220> FEATURE:
<221> NAME/KEY: DOMAIN
<222> LOCATION: (0)..(7)
<223> OTHER INFORMATION: mAb017 heavy chain CDR1

<400> SEQUENCE: 13

Gly Tyr Thr Phe Thr Thr Tyr
1               5

<210> SEQ ID NO 14
<211> LENGTH: 6
<212> TYPE: PRT
<213> ORGANISM: Artificial Sequence
<220> FEATURE:
<221> NAME/KEY: DOMAIN
<222> LOCATION: (0)..(6)
<223> OTHER INFORMATION: mAb017 heavy chain CDR2

<400> SEQUENCE: 14

Tyr Pro Arg Ser Gly Asn
1               5

<210> SEQ ID NO 15
<211> LENGTH: 10
<212> TYPE: PRT
<213> ORGANISM: Artificial Sequence
<220> FEATURE:
<221> NAME/KEY: DOMAIN
<222> LOCATION: (0)..(10)
<223> OTHER INFORMATION: mAb017 heavy chain CDR3

<400> SEQUENCE: 15

Gly Ser Asp Tyr Asp Gly Asp Phe Ala Tyr
1               5                   10

<210> SEQ ID NO 16
<211> LENGTH: 16
<212> TYPE: PRT
<213> ORGANISM: Artificial Sequence
<220> FEATURE:
<221> NAME/KEY: DOMAIN
<222> LOCATION: (0)..(16)
<223> OTHER INFORMATION: mAb017 light chain CDR1

<400> SEQUENCE: 16

Arg Ser Ser Gln Ser Ile Val His His Asp Gly Asn Thr Tyr Leu Glu
1               5                   10                  15

<210> SEQ ID NO 17
<211> LENGTH: 117
<212> TYPE: PRT
<213> ORGANISM: Artificial Sequence
<220> FEATURE:
<221> NAME/KEY: CHAIN
<222> LOCATION: (0)..(117)
<223> OTHER INFORMATION: mAb016 heavy chain variable region

<400> SEQUENCE: 17

Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Ile Phe Thr Asn Tyr
                20                  25                  30

Gly Ile Ile Trp Val Lys Gln Arg Thr Gly Gln Gly Leu Glu Trp Ile
            35                  40                  45

Gly Asp Ile Phe Pro Gly Ser Gly Asn Thr Tyr Tyr Asn Glu Asn Phe
        50                  55                  60

Lys Gly Lys Ala Thr Leu Thr Ala Asp Lys Ser Ser Ser Thr Ala Tyr
65                  70                  75                  80

Met Glu Leu Arg Ser Leu Thr Ser Glu Asp Ser Ala Val Tyr Phe Cys
                85                  90                  95

Ser Arg Gly Glu Leu Gly Asp Phe Asp Tyr Trp Gly Gln Gly Thr Thr
            100                 105                 110

Leu Thr Val Ser Ser
        115

<210> SEQ ID NO 18
<211> LENGTH: 112
<212> TYPE: PRT
<213> ORGANISM: Artificial Sequence
<220> FEATURE:
<221> NAME/KEY: CHAIN
<222> LOCATION: (0)..(112)
<223> OTHER INFORMATION: mAb016 light chain variable region

<400> SEQUENCE: 18

Val Val Leu Met Thr Gln Thr Pro Leu Ser Leu Pro Val Ser Leu Gly
1               5                   10                  15

Asp Gln Ala Ser Ile Ser Cys Arg Ser Ser Gln Asn Ile Val His Ser
                20                  25                  30

Asp Gly Thr Thr Tyr Leu Glu Trp Tyr Leu Gln Lys Pro Gly Gln Ser
            35                  40                  45

Pro Lys Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile

```
65                  70                  75                  80
Ser Arg Val Glu Ala Glu Asp Leu Gly Ile Tyr Tyr Cys Phe Gln Gly
                85                  90                  95

Ser His Val Pro Trp Thr Phe Gly Gly Gly Thr Lys Leu Glu Ile Lys
            100                 105                 110

<210> SEQ ID NO 19
<211> LENGTH: 447
<212> TYPE: PRT
<213> ORGANISM: Artificial Sequence
<220> FEATURE:
<221> NAME/KEY: CHAIN
<222> LOCATION: (0)..(447)
<223> OTHER INFORMATION: hAb015 humanized antibody heavy chain sequence

<400> SEQUENCE: 19

Glu Val Gln Leu Val Gln Ser Gly Ala Glu Val Lys Lys Pro Gly Ser
1               5                   10                  15

Ser Val Lys Val Ser Cys Lys Ala Ser Gly Ser Ser Phe Ser Ser Tyr
            20                  25                  30

Gly Ile Asn Trp Val Lys Gln Ala Pro Gly Gln Gly Leu Glu Trp Ile
        35                  40                  45

Gly Glu Ile Phe Pro Arg Ser Gly Asn Thr Tyr Tyr Asn Glu Lys Phe
    50                  55                  60

Glu Gly Arg Ala Thr Leu Thr Ala Asp Lys Ser Thr Ser Thr Ala Tyr
65                  70                  75                  80

Met Glu Leu Arg Ser Leu Arg Ser Glu Asp Thr Ala Val Tyr Tyr Cys
                85                  90                  95

Ala Lys Gly Asp Leu Gly Asp Phe Asp Tyr Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320
```

Cys Lys Val Ser Asn Lys Ala Leu Pro Ala Pro Ile Glu Lys Thr Ile
            325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
            370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
            405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
            435                 440                 445

<210> SEQ ID NO 20
<211> LENGTH: 219
<212> TYPE: PRT
<213> ORGANISM: Artificial Sequence
<220> FEATURE:
<221> NAME/KEY: CHAIN
<222> LOCATION: (0)..(219)
<223> OTHER INFORMATION: hAb015 humanized antibody light chain sequence

<400> SEQUENCE: 20

Asp Phe Val Met Thr Gln Thr Pro Leu Ser Leu Pro Val Thr Pro Gly
1               5                   10                  15

Glu Pro Ala Ser Ile Ser Cys Arg Ser Ser Gln Ser Ile Val His Ser
            20                  25                  30

Asp Gly Asn Thr Tyr Phe Glu Trp Tyr Leu Gln Lys Pro Gly Gln Ser
            35                  40                  45

Pro Lys Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
            85                  90                  95

Ser His Val Pro Trp Thr Phe Gly Gly Gly Thr Lys Val Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
            165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
        210                 215

<210> SEQ ID NO 21
<211> LENGTH: 449
<212> TYPE: PRT
<213> ORGANISM: Artificial Sequence
<220> FEATURE:
<221> NAME/KEY: CHAIN
<222> LOCATION: (0)..(449)
<223> OTHER INFORMATION: hAb017 humanized antibody heavy chain sequence

<400> SEQUENCE: 21

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Gly Ile Asn Trp Val Lys Gln Ala Pro Gly Gln Gly Leu Glu Trp Ile
        35                  40                  45

Gly Glu Ile Tyr Pro Arg Ser Gly Asn Ile Tyr Tyr Asn Glu Lys Phe
    50                  55                  60

Lys Gly Lys Ala Thr Leu Thr Ala Asp Lys Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Ser Asp Tyr Asp Gly Asp Phe Ala Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
```

```
              355                 360                 365
Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 22
<211> LENGTH: 219
<212> TYPE: PRT
<213> ORGANISM: Artificial Sequence
<220> FEATURE:
<221> NAME/KEY: CHAIN
<222> LOCATION: (0)..(219)
<223> OTHER INFORMATION: hAb017 humanized antibody light chain sequence

<400> SEQUENCE: 22

Asp Val Val Met Thr Gln Thr Pro Leu Ser Leu Pro Val Thr Pro Gly
1               5                   10                  15

Glu Pro Ala Ser Ile Ser Cys Arg Ser Ser Gln Ser Ile Val His His
            20                  25                  30

Asp Gly Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Trp Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 23
<211> LENGTH: 7
<212> TYPE: PRT
<213> ORGANISM: Artificial Sequence
<220> FEATURE:
```

```
<221> NAME/KEY: DOMAIN
<222> LOCATION: (0)..(7)
<223> OTHER INFORMATION: mAb016 heavy chain CDR1

<400> SEQUENCE: 23

Gly Tyr Ile Phe Thr Asn Tyr
1               5

<210> SEQ ID NO 24
<211> LENGTH: 6
<212> TYPE: PRT
<213> ORGANISM: Artificial Sequence
<220> FEATURE:
<221> NAME/KEY: DOMAIN
<222> LOCATION: (0)..(6)
<223> OTHER INFORMATION: mAb016 heavy chain CDR2

<400> SEQUENCE: 24

Phe Pro Gly Ser Gly Asn
1               5

<210> SEQ ID NO 25
<211> LENGTH: 8
<212> TYPE: PRT
<213> ORGANISM: Artificial Sequence
<220> FEATURE:
<221> NAME/KEY: DOMAIN
<222> LOCATION: (0)..(8)
<223> OTHER INFORMATION: mAb016 heavy chain CDR3

<400> SEQUENCE: 25

Gly Glu Leu Gly Asp Phe Asp Tyr
1               5

<210> SEQ ID NO 26
<211> LENGTH: 16
<212> TYPE: PRT
<213> ORGANISM: Artificial Sequence
<220> FEATURE:
<221> NAME/KEY: DOMAIN
<222> LOCATION: (0)..(16)
<223> OTHER INFORMATION: mAb016 light chain CDR1

<400> SEQUENCE: 26

Arg Ser Ser Gln Asn Ile Val His Ser Asp Gly Thr Thr Tyr Leu Glu
1               5                   10                  15
```

ANTI-CD79B ANTIBODY, ANTIGEN-BINDING FRAGMENT THEREOF, AND PHARMACEUTICAL USE THEREOF

CROSS-REFERENCE TO RELATED APPLICATIONS

This application is a U.S. National Phase of International PCT Application No. PCT/CN2020/073803, which was filed on Jan. 22, 2020, and which claims the priority of the Chinese Patent Application Serial No. 201910083330.4, which was filed on Jan. 28, 2019 and is entitled "Anti-CD79B antibody, antigen-binding fragment thereof, and pharmaceutical use thereof." The contents of each application are incorporated herein by reference in their entireties.

SEQUENCE LISTING

This application incorporates by reference the material in the ASCII file titled CHENG-23_Sequence-Listing, which was created on Mar. 12, 2025 and is 27,662 bytes.

FIELD OF THE INVENTION

The present invention relates to an anti-human CD79B antibody and antigen-binding fragment, a chimeric antibody and a humanized antibody comprising CDR region(s) of the anti-CD79B antibody, a pharmaceutical composition comprising the anti-human CD79B antibody or the antigen-binding fragment thereof, as well as a use thereof as an anti-cancer drug, particularly as a drug for treating lymphoma (DLBCL).

BACKGROUND OF THE INVENTION

Malignant tumor (cancer) is the second leading cause of death in the world, just ranking after heart disease. Lymphoma is a malignant tumor that originates from the lymphoid hematopoietic system and is the most common hematological tumor in the world. The incidence of lymphoma in China has been on the rise in recent years, and the current incidence is about 6.68 cases per 100,000 people.

Lymphoma is divided into two types, non-Hodgkin's lymphoma (NHL) and Hodgkin's lymphoma (HL). Non-Hodgkin's lymphoma is a general term for a group of abnormal lymphocyte proliferation diseases with strong heterogeneity. Its incidence is much higher than Hodgkin's lymphoma, accounting for more than 80% of lymphomas. Among them, diffuse large B-cell lymphoma (DLBCL) is the most common type of lymphoma in adults, accounting for about 32.5% of all non-Hodgkin's lymphomas; in Asian population, this proportion is even higher, close to 40%. It is more common in elderly patients, with a median age of onset of 60-64 years old. Male patients are slightly more than female patients.

Currently, the first-line standard regimen for diffuse large B-cell lymphoma (DLBCL) is rituximab combined with chemotherapy (R-CHOP). Before rituximab was marketed, the anthracycline-based CHOP (cyclophosphamide, doxorubicin, vincristine and prednisone) regimen was the first-line standard treatment regimen for DLBCL. The R-CHOP treatment regimen has significantly improved the long-term survival rate of DLBCL patients. The clinical trial results show that: compared with the traditional CHOP regimen, the R-CHOP regimen can significantly prolong the median overall survival time of patients with DLBCL by 4.9 years, the median disease-free survival time by more than 6.6 years, and the 5-year disease-free survival rate has increased from 30% to 54%. However, there are still 10% to 15% of refractory patients who do not respond, and 20% to 30% of patients have relapses. And not all DLBCL patients are suitable for R-CHOP regimen, such as elderly patients over 80 years old whose physical fitness does not allow standard R-CHOP treatment; another example is that for more aggressive types of lymphoma and recurrent lymphoma, the R-CHOP regimen may be invalid. Therefore, it is extremely necessary to develop new generation of immunotherapies with fewer side effects for the treatment of DLBCL.

According to the classification of lymphocytes by origin, diffuse large B-cell lymphoma (DLBCL) belongs to B-cell lymphoma. The B cell receptor (BCR) complex is the most major molecule on the surface of B cells. The BCR complex consists of membrane immunoglobulin (mIg) that recognizes and binds antigen and Igα (CD79a) and Igβ (CD79B) heterodimers that transmit antigen stimulation signals. Igα and Igβ are 47 kDa and 37 kDa glycoproteins, respectively, and belong to the immunoglobulin superfamily. The genes encoding Igα and Igβ are called mb-1 and B29, respectively. Both Igα and Igβ have an Ig-like domain at the amino terminus of the extracellular region. Both Igα and Igβ can be used as substrates of protein tyrosine kinases and participate in BCR signal transduction. BCR is widely expressed on B-cell lymphomas and normal B cells. In view of the clinical success and reliable safety of rituximab targeting CD20, the development of therapeutic methods targeting BCR should also have good curative effect and safety.

In response to the unmet medical needs related to CD79B, many international pharmaceutical companies, including Roche Pharmaceuticals, are actively developing antibodies against CD79B and related products. Related patents are such as U.S. Pat. No. 9,085,630, WO2009012256, WO2009012268, WO2009099728, WO2014011519, WO2014011521, WO2016090210, WO2016205176, WO2016040856, WO2016021621, WO2017009474, WO2014177615, etc.

Based on the expression of CD79B, it is beneficial to generate therapeutic antibodies against the CD79B antigen. There is still an unmet need in the art for the development of effective anti-human CD79B antibodies for treating hematopoietic tumors or delaying the progress.

SUMMARY OF THE INVENTION

The present disclosure provides an anti-CD79B antibody or antigen-binding fragment thereof, a nucleic acid encoding the same, a vector, a host cell, an antibody-drug conjugate and a pharmaceutical composition thereof, and a method using the same for treating or delaying cancer, especially hematopoietic tumors.

In the first aspect, the present disclosure provides an anti-human CD79B antibody or antigen-binding fragment thereof, which comprises an antibody heavy chain variable region and an antibody light chain variable region, wherein:
  the antibody heavy chain variable region comprises at least one complementarity determining region (HCDR) as shown in sequences selected from the following: SEQ ID NO: 7, SEQ ID NO: 8, SEQ ID NO: 9, SEQ ID NO: 13, SEQ ID NO: 14, SEQ ID NO: 15, SEQ ID NO: 23, SEQ ID NO: 24 and SEQ ID NO: 25; and/or
  the variable region of an antibody light chain comprises at least one complementarity determining region(LCDR) as shown in sequences selected from the following: SEQ ID NO: 10, SEQ ID NO: 11, SEQ ID NO: 12, SEQ ID NO: 16 and SEQ ID NO: 26.

In some embodiments, provided is an anti-human CD79B antibody or antigen-binding fragment thereof, wherein:
the heavy chain variable region comprises:
(I) HCDR1, HCDR2 and HCDR3 as shown in SEQ ID NO: 7, SEQ ID NO: 8 and SEQ ID NO: 9, respectively; or
(II) HCDR1, HCDR2 and HCDR3 as shown in SEQ ID NO: 13, SEQ ID NO: 14 and SEQ ID NO: 15, respectively; or
(III) HCDR1, HCDR2 and HCDR3 as shown in SEQ ID NO: 23, SEQ ID NO: 24 and SEQ ID NO: 25, respectively;
and/or the light chain variable region comprises:
(I) LCDR1, LCDR2 and LCDR3 as shown in SEQ ID NO: 10, SEQ ID NO: 11 and SEQ ID NO: 12, respectively; or
(II) LCDR1, LCDR2 and LCDR3 as shown in SEQ ID NO: 16, SEQ ID NO: 11 and SEQ ID NO: 12, respectively; or
(III) LCDR1, LCDR2 and LCDR3 as shown in SEQ ID NO: 26, SEQ ID NO: 11 and SEQ ID NO: 12, respectively.

In some specific embodiments, provided is an anti-human CD79B antibody or antigen-binding fragment thereof, which comprises any one selected from of the following (I) to (III):
(I) a heavy chain variable region, comprising HCDR1, HCDR2 and HCDR3 as shown in SEQ ID NO: 7, SEQ ID NO: 8 and SEQ ID NO: 9, respectively; and
a light chain variable region, comprising LCDR1, LCDR2 and LCDR3 as shown in SEQ ID NO: 10, SEQ ID NO: 11 and SEQ ID NO: 12, respectively;
(II) a heavy chain variable region, comprising HCDR1, HCDR2 and HCDR3 as shown in SEQ ID NO: 13, SEQ ID NO: 14 and SEQ ID NO: 15, respectively; and
a light chain variable region, comprising LCDR1, LCDR2 and LCDR3 as shown in SEQ ID NO: 16, SEQ ID NO: 11 and SEQ ID NO: 12, respectively;
(III) a heavy chain variable region, comprising HCDR1, HCDR2 and HCDR3 as shown in SEQ ID NO: 23, SEQ ID NO: 24 and SEQ ID NO: 25, respectively; and
a light chain variable region, comprising LCDR1, LCDR2 and LCDR3 as shown in SEQ ID NO: 26, SEQ ID NO: 11 and SEQ ID NO: 12, respectively.

In some specific embodiments, provided is an anti-human CD79B antibody or antigen-binding fragment thereof, wherein:
the heavy chain variable region comprises:
(I) the sequence as shown in SEQ ID NO: 3 or the sequence with at least 80%, 85%, 90%, 95%, 96%, 97%, 98% or 99% identity with SEQ ID NO: 3; or
(II) the sequence as shown in SEQ ID NO: 5 or the sequence with at least 80%, 85%, 90%, 95%, 96%, 97%, 98% or 99% identity with SEQ ID NO: 5; or
(III) the sequence as shown in SEQ ID NO: 17 or the sequence with at least 80%, 85%, 90%, 95%, 96%, 97%, 98% or 99% identity with SEQ ID NO: 17;
and/or the light chain variable region comprises:
(I) the sequence as shown in SEQ ID NO: 4 or the sequence with at least 80%, 85%, 90%, 95%, 96%, 97%, 98% or 99% identity with SEQ ID NO: 4; or
(II) the sequence as shown in SEQ ID NO: 6 or the sequence with at least 80%, 85%, 90%, 95%, 96%, 97%, 98% or 99% identity with SEQ ID NO: 6; or
(III) the sequence as shown in SEQ ID NO: 18 or the sequence with at least 80%, 85%, 90%, 95%, 96%, 97%, 98% or 99% identity with SEQ ID NO: 18.

In some specific embodiments, the heavy chain variable region of the anti-human CD79B antibody or antigen-binding fragment is as shown in SEQ ID NO: 3, and the light chain variable region is as shown in SEQ ID NO: 4.

In some other specific embodiments, the heavy chain variable region of the anti-human CD79B antibody or antigen-binding fragment is as shown in SEQ ID NO: 5, and the light chain variable region is as shown in SEQ ID NO: 6.

In some other specific embodiments, the heavy chain variable region of the anti-human CD79B antibody or antigen-binding fragment is as shown in SEQ ID NO: 17, and the light chain variable region is as shown in SEQ ID NO: 18.

In some specific embodiments, the anti-human CD79B antibody or antigen-binding fragment thereof, wherein:
the heavy chain comprises:
(I) the sequence as shown in SEQ ID NO: 19 or the sequence with at least 80%, 85%, 90%, 95%, 96%, 97%, 98% or 99% identity with SEQ ID NO: 19; or
(II) the sequence as shown in SEQ ID NO: 21 or the sequence with at least 80%, 85%, 90%, 95%, 96%, 97%, 98% or 99% identity with SEQ ID NO: 21; or
and/or the light chain comprises:
(I) the sequence as shown in SEQ ID NO: 20 or the sequence with at least 80%, 85%, 90%, 95%, 96%, 97%, 98% or 99% identity with SEQ ID NO: 20; or
(II) the sequence as shown in SEQ ID NO: 22 or the sequence with at least 80%, 85%, 90%, 95%, 96%, 97%, 98% or 99% identity with SEQ ID NO: 22;

In some specific embodiments, the heavy chain of the anti-human CD79B antibody or antigen-binding fragment is as shown in SEQ ID NO: 19, and the light chain is as shown in SEQ ID NO: 20.

In some other specific embodiments, the heavy chain of the anti-human CD79B antibody or antigen-binding fragment is as shown in SEQ ID NO: 21, and the light chain is as shown in SEQ ID NO: 22.

In some embodiments, provided is the anti-human CD79B antibody or antigen-binding fragment thereof as described above, which is a murine antibody or fragment thereof.

In some specific embodiments, the light chain variable region of the murine anti-CD79B antibody or antigen-binding fragment thereof comprises the light chain FR region and/or the light chain constant region of murine κ, λ chain or variant thereof.

In some specific embodiments, the murine anti-CD79B antibody or antigen-binding fragment thereof comprises the heavy chain FR region and/or the heavy chain constant region of murine IgG1, IgG2, IgG3, IgG4 or variant thereof.

In some embodiments, provided is the anti-human CD79B antibody or antigen-binding fragment thereof as described above, which is a chimeric antibody or fragment thereof. In some specific embodiments, the chimeric anti-CD79B antibody or antigen-binding fragment thereof comprises the light chain FR region and/or the light chain constant region of human κ, λ chain or variant thereof, and/or the heavy chain FR region and/or the heavy chain constant region of human IgG1, IgG2, IgG3, IgG4 or variant thereof.

In some embodiments, provided is the anti-human CD79B antibody or antigen-binding fragment thereof as described above, which is a humanized antibody, a human antibody or fragment thereof.

In some embodiments, provided is the anti-human CD79B humanized antibody or antigen-binding fragment thereof as described above, wherein the light chain sequence is shown in SEQ ID NO: 20 or variant sequence thereof, the variant sequence comprises 1, 2, 3, 4, 5, 6, 7, 8, 9 or 10 amino acid change(s) in the light chain, or has at least 80%, 85%, 90%, 95%, 96%, 97%, 98% or 99% identity with SEQ ID NO: 20. The heavy chain sequence is shown in SEQ ID NO: 19 or variant sequence thereof, the variant sequence comprises 1, 2, 3, 4, 5, 6, 7, 8, 9 or 10 amino acid change(s) in the heavy chain, or has at least 80%, 85%, 90%, 95%, 96%, 97%, 98% or 99% identity with SEQ ID NO: 19.

In some embodiments, provided is the anti-human CD79B humanized antibody or antigen-binding fragment thereof as described above, wherein the light chain sequence is shown in SEQ ID NO: 22 or variant sequence thereof, or has at least 80%, 85%, 90%, 95%, 96%, 97%, 98% or 99% identity with SEQ ID NO: 22; the variant sequence comprises 1, 2, 3, 4, 5, 6, 7, 8, 9 or 10 amino acid change(s) in the light chain. The heavy chain sequence is shown in SEQ ID NO: 21 or variant sequence thereof, the variant sequence comprises 1, 2, 3, 4, 5, 6, 7, 8, 9 or 10 amino acid change(s) in the heavy chain, or has at least 80%, 85%, 90%, 95%, 96%, 97%, 98% or 99% identity with SEQ ID NO: 21.

In some embodiments, the anti-CD79B human antibody or fragment thereof as described above, which further comprises the constant region of human IgG1, IgG2, IgG3 or IgG4 or variant thereof. In some specific embodiments, the anti-CD79B human antibody or fragment thereof comprises the constant region of human IgG1 or IgG2.

In some embodiments, the anti-human CD79B humanized antibody or fragment thereof as described above, which further comprises the heavy chain constant region of human IgG1, IgG2, IgG3 or IgG4 or variant thereof, preferably comprising human IgG1, IgG2 or IgG4 heavy chain FR region, more preferably comprising human IgG1 or IgG2 heavy chain FR region.

In some embodiments, the anti-human CD79B antibody or antigen-binding fragment thereof as described above, wherein the antigen-binding fragment is selected from the group consisting of Fab, Fv, sFv, F(ab')2, linear antibody, single-chain antibody, scFv, sdAb, sdFv, nanobody, peptibody, domain antibody and multispecific antibody (bispecific antibody, diabody, triabody and tetrabody, tandem di-scFv and tandem tri-scFv.

In some embodiments, provided is an isolated monoclonal antibody or antigen-binding fragment thereof, which can compete with the aforementioned monoclonal antibody or antigen-binding fragment thereof for binding to human CD79B or epitope thereof.

The amino acid residues of the VH/VL CDR of the anti-human CD79B antibody in the present disclosure are determined and annotated by the Chothia numbering system.

In the second aspect, the present disclosure provides a polynucleotide encoding the anti-human CD79B antibody or antigen-binding fragment thereof as described above, which can be DNA or RNA.

In the third aspect, the present disclosure provides an expression vector comprising the polynucleotide as described above, which can be a eukaryotic expression vector, a prokaryotic expression vector or a viral vector.

In a fourth aspect, the present disclosure provides a host cell transformed with the expression vector as described above, which can be a eukaryotic cell or a prokaryotic cell.

In some embodiments, the host cell is a bacterium, yeast or mammalian cell. In some specific embodiments, the host cell is *Escherichia coli*, *Pichia pastoris*, Chinese hamster ovary (CHO) cell or human embryonic kidney (HEK) 293 cell.

In a fifth aspect, the present disclosure provides an antibody-drug conjugate.

The antibody-drug conjugate according to the present disclosure comprises or consists of the following: antibody, linker and drug.

In a specific embodiment, the antibody-drug conjugate according to the present disclosure is an antibody covalently coupled to a drug through a linker.

In some embodiments, the antibody-drug conjugate contains a cytotoxic agent. In some specific embodiments, the cytotoxic agent is selected from the group consisting of toxin, chemotherapeutic, antibiotic, radioisotope and nucleolytic enzyme.

In the sixth aspect, the present disclosure provides a method for preparing the anti-human CD79B antibody or antigen-binding fragment thereof, comprising: expressing the antibody or antigen-binding fragment thereof in the host cell as described above, and isolating the antibody or antigen-binding fragment thereof from the host cell.

In the seventh aspect, the present disclosure provides a composition, for example a pharmaceutical composition, which contains a therapeutically effective amount of the aforementioned anti-human CD79B antibody or antigen-binding fragment thereof and a pharmaceutically acceptable excipient, diluent or carrier.

In some specific embodiments, the unit dose of the pharmaceutical composition comprises 0.01% to 99% by weight of the anti-human CD79B antibody or antigen-binding fragment thereof, or the amount of the anti-CD79B antibody or antigen-binding fragment thereof in the unit dose of the pharmaceutical composition is 0.1 mg to 2000 mg, and in some specific embodiments 1 mg to 1000 mg.

In the eighth aspect, the present disclosure further provides the use of any one or a combination selected from the following in the preparation of medicament: the anti-human CD79B antibody or antigen-binding fragment thereof according to the present disclosure, the pharmaceutical composition according to the present disclosure, the antibody-drug conjugate according to the present disclosure; wherein the medicament or the pharmaceutical composition is used to treat a proliferative disease or to delay the progression of a proliferative disease; said proliferative disease can be cancer or tumor. In some embodiments, the cancer or tumor is lymphoma or leukemia. In a specific embodiment, the lymphoma is selected from the group consisting of: diffuse large B-cell lymphoma, non-Hodgkin's lymphoma, small lymphocytic lymphoma and mantle cell lymphoma. In a specific embodiment, the non-Hodgkin's lymphoma is selected from the group consisting of: aggressive NHL, recurrent aggressive NHL, recurrent painless NHL, refractory NHL and refractory painless NHL. In a specific embodiment, the leukemia is selected from the group consisting of: chronic lymphocytic leukemia, hairy cell leukemia and acute lymphocytic leukemia.

In the ninth aspect, the present disclosure further provides a method for treating or preventing a proliferative disease or for delaying the progression of a proliferative disease, which comprises administrating to a subject a therapeutically effective amount or disease-delaying effective amount of the anti-human CD79B antibody or antigen-binding fragment thereof according to the present disclosure, or the pharmaceutical composition according to the present disclosure, or the antibody-drug conjugate according to the present disclosure; wherein, the proliferative disease can be cancer or tumor. In some embodiments, the cancer or tumor is lymphoma or leukemia. In a specific embodiment, the lymphoma is selected from the group consisting of: diffuse large B-cell lymphoma, non-Hodgkin's lymphoma, small lymphocytic lymphoma and mantle cell lymphoma. In a specific embodiment, the non-Hodgkin's lymphoma is selected from the group consisting of: aggressive NHL, recurrent aggressive NHL, recurrent painless NHL, refractory NHL and refractory painless NHL. In a specific embodiment, the leukemia is selected from the group consisting of: chronic lymphocytic leukemia, hairy cell leukemia and acute lymphocytic leukemia.

DETAILED DESCRIPTION OF THE INVENTION

Terms

Figure 1:
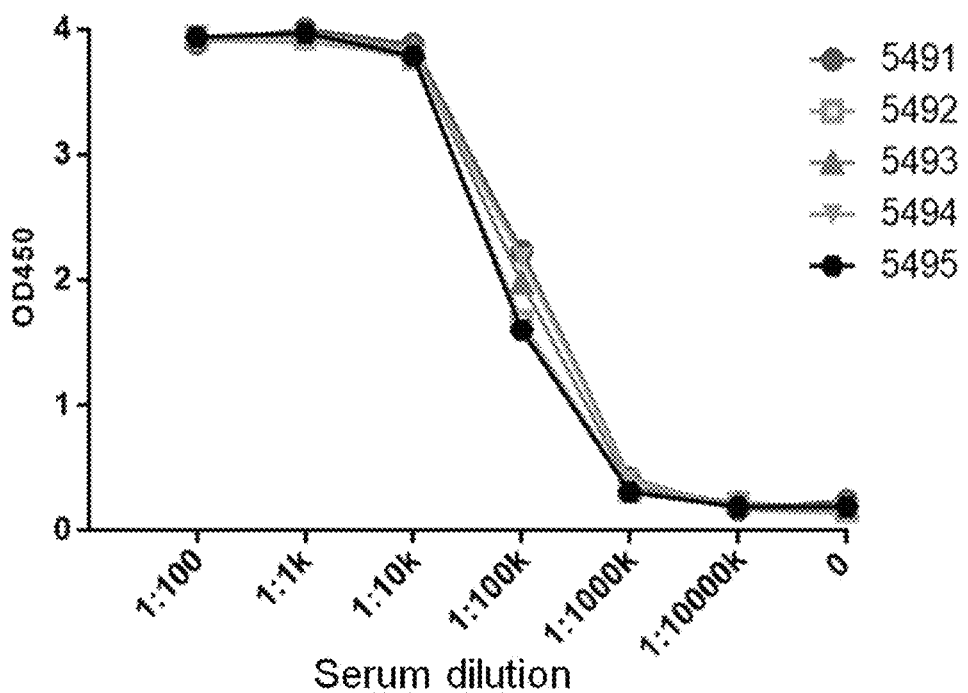
FIG. 1: ELISA detection results of serum titer of Balb/c mice immunized with human CD79B ECD-hFc protein.

To make it easier to understand the present disclosure, certain technical and scientific terms are specifically defined below. Unless otherwise clearly defined elsewhere in this document, all other technical and scientific terms used herein have the meanings commonly understood by those of ordinary skill in the art to which the present disclosure pertains.

The three-letter codes and one-letter codes of amino acids used in the present disclosure are as described in J. Biol. Chem, 243, p3558 (1968).

"CD79B" refers to any CD79B of any vertebrate origin, including mammal, such as primate (for example human and *Macaca* monkey (cyno)) and rodent (for example mouse and rat). The term "CD79B" encompasses "full length", unprocessed CD79B and any form of CD79B processed from cells. The term also encompasses naturally occurring CD79B variants, for example splice variants, allelic variants and isoforms. The CD79B polypeptides described herein can be isolated from a variety of sources, such as human tissue types or other sources, or prepared by recombinant or synthetic methods.

The term "antibody" described in the present disclosure refers to an immunoglobulin, which is a tetrapeptide chain structure composed of two identical heavy chains and two identical light chains linked by interchain disulfide bond(s).

The amino acid composition and sequence of the immunoglobulin heavy chain constant region are different, so their antigenicity is also different. According to this, immunoglobulins can be divided into five types, or isotypes of immunoglobulins, namely IgM, IgD, IgG, IgA and IgE, and their corresponding heavy chains are μ chain, δ chain, γ chain, α chain and ε chain, respectively. The same type of Ig can be divided into different subclasses according to the difference in the amino acid composition of the hinge region and the number and position of heavy chain disulfide bonds. For example, IgG can be divided into IgG1, IgG2, IgG3 and IgG4. The light chain is divided into κ chain or λ chain by the difference of the constant region. Each of the five types of Ig can have a κ chain or a λ chain. The sequence of about 110 amino acids near the N-terminus of the antibody heavy and light chains varies greatly and is named as variable region (V region); the remaining amino acid sequence near the C-terminus is relatively stable and is named as constant region (C region). The variable region includes 3 hypervariable regions (HVR) and 4 framework regions (FR) with relatively conservative sequences. The 3 hypervariable regions determine the specificity of the antibody, and is also known as complementarity determining regions (CDR). Each light chain variable region (VL) and heavy chain variable region (VH) consists of 3 CDR regions and 4 FR regions. The sequence from the amino terminal to the carboxy terminal is: FR1, CDR1, FR2, CDR2, FR3, CDR3 and FR4. The 3 CDR regions of the light chain refer to LCDR1, LCDR2 and LCDR3; the 3 CDR regions of the heavy chain refer to HCDR1, HCDR2 and HCDR3. The number and position of the VL region and VH region CDR amino acid residues of the antibody or antigen-binding fragment comply with the known Chothia (ABM) numbering rules.

The term "human antibody" or "recombinant human antibody" includes human antibodies prepared, expressed, created or isolated by recombinant methods, and the techniques and methods involved are well known in the art, such as:

(1) antibodies isolated from transgenic and transchromosomal animals (for example mice) of human immunoglobulin genes, or from hybridomas prepared therefrom;
(2) antibodies isolated from host cells (such as transfectionomas) transformed to express the antibodies;
(3) antibodies isolated from the recombinant combinatorial human antibody library; and
(4) antibodies prepared, expressed, created or isolated by other techniques which are used for splicing human immunoglobulin gene sequences into other DNA sequences.

Such recombinant human antibodies contain variable regions and constant regions, which utilize specific human germline immunoglobulin sequences encoded by germline genes, but also include subsequent rearrangements and mutations such as those occur during antibody maturation.

The term "murine antibody" in the present disclosure is a monoclonal antibody against human CD79B or epitope thereof prepared according to the knowledge and skills in the art. During preparation, the test subject is injected with CD79B antigen or epitope thereof, and then hybridomas expressing antibodies with the desired sequence or functional properties are isolated. In a specific embodiment of the present disclosure, the murine anti-CD79B antibody or antigen-binding fragment thereof may further comprise the light chain constant region of murine κ, λ chain or variant thereof, or further comprise the heavy chain constant region of murine IgG1, IgG2, IgG3 or IgG4 or variant thereof.

The term "human antibody" includes antibodies having variable and constant regions of human germline immunoglobulin sequences. The human antibodies of the present disclosure may include amino acid residues that are not encoded by human germline immunoglobulin sequences (such as mutations introduced by random or site-specific mutagenesis in vitro or by somatic mutations in vivo). However, the term "human antibody" does not include antibodies in which CDR sequences derived from the germline of another mammalian species (such as a mouse) have been grafted onto human framework sequences (namely "humanized antibodies").

The term "humanized antibody", also known as CDR-grafted antibody, refers to the antibody produced by transplanting CDR sequences of non-human species into the framework of human antibody variable regions. It can overcome the strong immune response reactions induced by the chimeric antibody as it carries a large amount of protein components of non-human species. In order to avoid the decrease in activity caused by the decrease in immunogenicity, the human antibody variable region can be subjected to minimal reverse mutations to maintain activity.

The term "chimeric antibody" is an antibody formed by fusing the antibody variable region of a first species with the antibody constant region of a second species, which can alleviate the immune response induced by antibody of the first species. Establishing a chimeric antibody requires establishing a hybridoma secreting specific monoclonal antibodies of the first species, then cloning the variable region gene from the hybridoma cells of the first species (such as mouse), and then cloning the antibody constant region gene of the second species (such as human), linking the variable region gene of the first species with the constant region gene of the second species to form a chimeric gene which is inserted into an expression vector, and finally expressing the chimeric antibody molecule in a eukaryotic industrial system or a prokaryotic industrial system. The antibody constant region of the second species (for example human) can be selected from the group consisting of: the heavy chain constant region of human IgG1, IgG2, IgG3, or IgG4 or variant thereof, preferably comprising human IgG2 or IgG4 heavy chain constant region, or using IgG1 without ADCC (antibody-dependent cell-mediated cytotoxicity) after amino acid mutations.

"Antigen-binding fragment" refers to any fragment that retains the antigen-binding activity of the intact antibody. Specifically, mention can be made of, but not limited to, Fab fragments, Fab' fragments, F(ab') 2 fragments, and Fv fragments or sFv fragments that bind to human CD79B. The Fv fragment contains the antibody heavy chain variable region and the light chain variable region, but does not have the constant region, and has the smallest antibody fragment with all antigen binding sites. Generally, the Fv antibody also contains a polypeptide linker between the VH and VL domains, and can form the structure required for antigen binding. Different linkers can also be used to link the two antibody variable regions into a polypeptide chain, which is called single chain antibody or single chain Fv (sFv).

The term "binding to CD79B" in the present disclosure refers to the ability to interact with CD79B or epitope thereof. The CD79B or epitope thereof can be of human origin. The term "antigen-binding site" in the present disclosure refers to a linear site or discontinuous three-dimensional site on the antigen, recognized by the antibody or antigen-binding fragment of the present disclosure.

The term "epitope" refers to a site on an antigen that specifically binds to an immunoglobulin or antibody. Epitopes can be formed by adjacent amino acids or non-adjacent amino acids that are brought close to each other by tertiary folding of the protein. Epitopes formed by adjacent amino acids are usually maintained after exposure to a denaturing solvent, while epitopes formed by tertiary folding are usually lost after treatment with a denaturing solvent. Epitopes usually include at least 3-15 amino acids in a unique spatial conformation. Methods to determine what epitope is bound by a given antibody are well known in the art, including immunoblotting, immunoprecipitation detection analysis, etc. Methods for determining the spatial conformation of an epitope include the techniques in the art and the techniques described herein, for example X-ray crystal analysis, two-dimensional nuclear magnetic resonance, etc.

"Specific binding" and "selective binding" refer to the binding of an antibody to an epitope on a predetermined antigen. Generally, when recombinant human CD79B or epitope thereof is used as an analyte and an antibody is used as a ligand, when measured by surface plasmon resonance (SPR) technology in an instrument, the antibody binds to the predetermined antigen or epitope thereof with a dissociation constant ($K_D$) of approximately below $10^{-7}$ M or even smaller, and its binding affinity to the predetermined antigen or epitope thereof is at least twice the binding affinity to non-specific antigens (such as BSA, etc.) other than the predetermined antigen (or epitope thereof) or closely related antigens.

"Cross-reaction" refers to the ability of the antibodies of the present disclosure binding to CD79B from different species. For example, an antibody of the present disclosure that binds to human CD79B can also bind to CD79B of another species. Cross-reactivity is measured by detecting specific reactivity with purified antigen in binding assays (for example SPR and ELISA), or binding or functional interaction with cells that physiologically express CD79B. Methods of determining cross-reactivity include standard binding assays as described herein, for example surface plasmon resonance analysis or flow cytometry.

"Inhibit" or "block" are used interchangeably and encompass both partial and complete inhibition/blocking. Inhibition/blocking of CD79B preferably reduces or alters the normal level or type of activity that occurs when CD79B binding occurs without inhibition or blocking. Inhibition and blocking are also intended to include any measurable reduction in binding affinity to CD79B when contacting with anti-CD79B antibody, compared to CD79B not contacting with anti-CD79B antibody.

"Inhibition of growth" (for example referring to cells) is intended to include any measurable decrease in cell growth.

The methods for producing and purifying antibodies or antigen-binding fragments are well-known and can be found in the prior art, such as Antibody: A Laboratory Manual, Cold Spring Harbor (chapters 5-8 and 15). For example, human CD79B or fragment thereof can be used to immunize mice, and the obtained antibodies can be renatured, purified, and amino acid sequencing can be performed by conventional methods. Antigen-binding fragments can also be prepared by conventional methods. The antibody or antigen-binding fragment of the invention is genetically engineered to introduce one or more human FR regions onto the non-human CDR regions. The human FR germline sequences can be obtained from the ImmunoGeneTics (IMGT) website http://imgt.cines.fr, or from The Immunoglobulin FactsBook, 2001ISBN012441351.

The engineered antibodies or antigen-binding fragments of the present disclosure can be prepared and purified by conventional methods. For example, the cDNA sequences encoding the heavy chain (SEQ ID NO: 20) and light chain (SEQ ID NO: 21) can be cloned and recombined into a GS expression vector. The recombinant immunoglobulin expression vector can be stably transfected into CHO cells. As a more recommended prior art, mammalian expression systems can lead to glycosylation of antibodies, especially at the highly conserved N-terminus of the Fc region. Stable clones are obtained by expressing antibodies that specifically bind to human antigens. Positive clones are expanded in the serum-free medium of the bioreactor to produce antibodies. The culture medium into which the antibodies are secreted can be purified and collected by conventional techniques. The antibodies can be filtered and concentrated by conventional methods. Soluble mixtures and polymers can also be removed by conventional methods, for example molecular sieves and ion exchange. The resulting product needs to be frozen immediately, such as −70° C., or lyophilized.

The antibody of the present disclosure refers to monoclonal antibody. The monoclonal antibody (mAb) described in the present disclosure refers to an antibody obtained from a single clone cell line, said cell line is not limited to a eukaryotic, prokaryotic or phage clone cell line. Monoclonal antibodies or antigen-binding fragments can be obtained by recombination using, for example, hybridoma technology, recombination technology, phage display technology, synthesis technology (such as CDR-grafting), or other existing technologies.

Conventional techniques known to those skilled in the art can be used to screen antibodies for competitive binding to the same epitope. For example, competition and cross-competition studies can be conducted to obtain antibodies that compete or cross-compete with each other for the binding to an antigen. A high-throughput method for obtaining antibodies that bind the same epitope based on their cross-competition is described in International Patent Publication WO03/48731. Therefore, conventional techniques known to those skilled in the art can be used to obtain antibodies and antigen-binding fragments thereof that compete with the antibody molecules of the present disclosure for binding to the same epitope on CD79B.

"Giving", "administering" and "treating", when applied to animals, humans, experimental subjects, cells, tissues, organs or biological fluids, refer to the contact of the exogenous medicament, therapeutic agent, diagnostic agent or composition with the animals, humans, subjects, cells, tissues, organs or biological fluids. "Giving", "administering" and "treating" can refer to for example treatment, pharmacokinetics, diagnosis, research and experimental methods. The treatment of cells includes contact of reagents with cells, and contact of reagents with fluid which in turn is in contact with the cells. "Giving", "administering" and "treating" also refer to treating for example cells by reagents, diagnosis, binding compositions or by another cell in vitro and ex vivo. "Treating" when applied to human, veterinary or research subjects, refers to therapeutic treatment, prophylactic treatment or prophylactic measures, research and diagnostic applications.

"Treatment" refers to giving an internal or external therapeutic agent, such as a composition comprising any one of the antibodies or antigen-binding fragments thereof of the present disclosure, to a subject who already has, is suspected to have or is susceptible to have one or more diseases or symptoms thereof, and the therapeutic agent is known to have therapeutic effect on said symptoms. Generally, the therapeutic agent is given in an amount effective to alleviate one or more disease symptoms in the treated subject or population, either to induce the regression of such symptoms or to inhibit the development of such symptoms to any clinically measured extent. The amount of therapeutic agent that is effective to alleviate any specific disease symptom (also referred to as a "therapeutically effective amount") can vary according to a variety of factors, for example the subject's disease state, age and body weight, and the ability of the drug to produce the desired therapeutic effect in the subject. Whether the disease symptoms have been alleviated can be evaluated through any clinical testing methods commonly used by doctors or other health care professionals to evaluate the severity or progression of the symptoms. Although the embodiments of the present disclosure (for example treatment methods or products) can be ineffective in alleviating the target disease symptom in a certain subject, but as determined according to any statistical test methods known in the art such as Student t test, chi-square test, Mann and Whitney's U test, Kruskal-Wallis test (H test), Jonckheere-Terpstra test and Wilcoxon test, they should reduce the target disease symptom in a statistically significant number of subjects.

The "effective amount" includes an amount sufficient to ameliorate or prevent the symptoms or conditions of the medical condition. The effective amount also refers to an amount sufficient to allow or facilitate diagnosis. The effective amount for a particular subject or veterinary subject can vary depending on the following factors: such as the condition to be treated, the general health condition of the subject, the method, route and dosage of administration, and the severity of side effects. The effective amount can be the maximum dose or dosing schedule that avoids significant side effects or toxic effects.

"Identity" refers to the sequence similarity between two polynucleotide sequences or between two polypeptides. When the positions in the two sequences compared are occupied by the same base or amino acid monomer subunit, for example if each position of two DNA molecules is occupied by adenine, then the molecules are homologous at that position. The identity percentage between two sequences is a function of the number of matching or homologous positions shared by the two sequences divided by the number of all positions to be compared ×100%. For example, in a the case of optimal sequence alignment, if there are 6 matches or homology in 10 positions in the two sequences, then the two sequences are 60% homologous. Generally speaking, the comparison is made when two sequences are aligned to obtain the maximum identity percentage.

The expressions "cell", "cell line" and "cell culture" as used herein can be used interchangeably, and all such names include progeny thereof. Therefore, the terms "transformant" and "transformed cell" include primary test cells and cultures derived therefrom, regardless of the number of passages. It should also be understood that due to intentional or unintentional mutations, all offspring cannot be exactly the same in terms of DNA content. The screened mutant progeny with the same function or biological activity as that of the original transformed cells is included in the scope of the term. When a term is referred to different indications, it would be obvious from the context.

"Optional" or "optionally" means that the described event or environment which follows the term"optional" can (but not necessarily) occur, and the description includes occasions where the event or environment occurs or does not occur. For example, "optionally comprising 1 to 3 antibody heavy chain variable regions" means that the antibody heavy chain variable regions of specific sequences may be (but not necessarily) present.

"Pharmaceutical composition" means a mixture comprising one or more of the antibodies or antigen-binding fragments, or conjugates described herein, or a physiologically/pharmaceutically acceptable salt or a prodrug thereof, and other chemical component(s), as well as other components such as physiological/pharmaceutically acceptable carrier(s) and excipient(s). The purpose of the pharmaceutical composition is to promote the administration to the organism, which facilitates the absorption of the active ingredient and thereby exerts biological activity.

EXAMPLES

The following examples are incorporated to further describe the disclosure, but these examples do not limit the scope.

The experimental methods that do not specify specific conditions in the Examples or Test Examples of the present disclosure usually follow conventional conditions, or the conditions recommended by the manufacturer of raw material or product. See Sambrook et al., Molecular Cloning: A Laboratory Manual, Cold Spring Harbor; Current Protocols Molecular Biology, Ausubel et al., Greene Publishing Associates, Wiley Interscience, NY The reagents without specific sources are the conventional reagents purchased on the market.

Example 1. Cloning and Expression of Protein Antigens

The antibodies (comprising light and heavy chains) and antigens were constructed by overlap extension PCR methods known in the art, and DNA fragments obtained by overlap extension PCR were inserted into the expression vector pEE6.4 (Lonza Biologics) by using the two enzyme cleavage sites HindIII/BstBI, and the antibodies and antigens were expressed in 293F cells (Invitrogen, Cat #R790-07). The obtained recombinant protein was used for immunization or screening. The human CD79B gene sequence is derived from NCBI (NP_000617.1), and its extracellular region (ECD) contains 159 amino acids (Met1-Asp159).
The amino acid sequence of the fusion protein of human CD79B extracellular domain (ECD) and human FC region (human CD79B ECD-hFc):

```
                                        (SEQ ID NO: 1)
ARSEDRYRNPKGSACSRIWQSPRFIARKRGFTVKMHCYMNSASGNVSWLWK

QEMDENPQQLKLEKGRMEESQNESLATLTIQGIRFEDNGIYFCQQKCNNTS

EVYQGCGTELRVMGFSTLAQLKQRNTLKDGIIMIQTLLIILFIIVPIFLLL

DKDDSKAGMEEDHTYEGLDIDQTATYEDIVTLRTGEVKWSVGEHPGQEEPK

SCDKTHTCPPCPAPELLGGPSVFLFPPKPKDTLMISRTPEVTCVVVDVSHE

DPEVKFNWYVDGVEVHNAKTKPREEQYNSTYRVVSVLTVLHQDWLNGKEYK

CKVSNKALPAPIEKTISKAKGQPREPQVYTLPPSREEMTKNQVSLTCLVKG

FYPSDIAVEWESNGQPENNYKTTPPVLDSDGSFFLYSKLTVDKSRWQQGNV

FSCSVMHEALHNHYTQKSLSLSPGK.
```

The amino acid sequence of the fusion protein of human CD79B extracellular domain (ECD) and His tag (human CD79B ECD-His):

```
                                        (SEQ ID NO: 2)
ARSEDRYRNPKGSACSRIWQSPRFIARKRGFTVKMHCYMNSASGNVSWLWK

QEMDENPQQLKLEKGRMEESQNESLATLTIQGIRFEDNGIYFCQQKCNNTS

EVYQGCGTELRVMGFSTLAQLKQRNTLKDGIIMIQTLLIILFIIVPIFLLL

DKDDSKAGMEEDHTYEGLDIDQTATYEDIVTLRTGEVKWSVGEHPGQEHHH

HHH.
```

Example 2. Preparation of Murine Monoclonal Antibodies

1. Immunization of Mouse and Detection of Serum Titer

The fusion protein of human CD79B extracellular domain (ECD) and human Fc region (human CD79B ECD-hFc), and the fusion protein of human CD79B extracellular region (ECD) and His tag (human CD79B ECD-His) were used as immunogens to immunize Balb/c and SJL mice by intraperitoneal injection, respectively, to stimulate the mice to produce antibodies against the extracellular domain (ECD) of human CD79B in vivo.

The experimental steps were as follows:

1) Immunization by intraperitoneal injection. The amount of antigen required for this immunization was calculated according to the immunization procedure. The protein antigen was diluted with PBS to the corresponding antigen concentration as required, and then the antigen was emulsified. The emulsified mixture of antigen and adjuvant was transferred to a 2.0 mL sterile syringe, paying attention to venting air bubbles. The tail of the mouse was grasped with the right hand and the skin of the head and neck of the mouse was gently grasped with the thumb and index finger of the left hand. With the abdominal cavity facing upwards, the injection site on the right abdomen of the mouse was wiped with 75% alcohol cotton ball. The antigen drug was loaded in advance into the syringe, with the bevel of the needle tip facing upwards and the head of the mouse facing downwards. The needle tip was pierced into the skin horizontally, the syringe was pierced into the abdominal cavity of the mouse at a 45-degree angle with the abdominal cavity, and the mixture of antigen and adjuvant was slowly injected. After the immunization was completed, observation was conducted for at least 2 h.

2) Collection of mouse serum. The numbers of serum tubes were marked corresponding to each mouse and the earring number of the mouse was checked. The mouse was grabbed with one hand and about 100 µl of whole blood was collected through the submandibular vein. The collected whole blood sample was let stand at room temperature for about 2 h; then the serum in the upper part of the centrifuge tube was collected by centrifugation. The serum could be stored in a refrigerator at 4° C. within one week for the detection of antibody titer and other related experiments. The serum could be stored in a refrigerator at −80° C. for long term storage to avoid repeated freezing and thawing.

3) ELISA serum titer detection of immunized mice. Before the start of the experiment, a 96-well plate was labeled accordingly and coated with antigen at a concentration of 1 µg/mL, 50 µl per well overnight in a refrigerator at 4° C. The next day, the antigen plate coated the day before was taken out and washed with a plate washer (washing solution: 1×PBST). After washing, the plate was blocked with 1% BSA blocking solution prepared in 1×PBST at 37° C. for 1 h. After washing the plate with 1×PBST washing solution for 3 times, different dilutions of serum to be tested were added and incubated in a 37° C. incubator for 1 h. After washing the plate with 1×PBST washing solution for 3 times, 100 μl 1:5000 diluted goat-anti-mouse secondary antibody was added and incubated in a 37° C. incubator for 0.5 h. After washing the plate, TMB chromogenic solution A and B were mixed at a 1:1 ratio and then color development was carried out. The development reaction was terminated with 1 N hydrochloric acid after 15 min. The fluorescence values at 450 nm were detected on a Spectra Max M5 multi-function plate reader.

4) FACS serum titer detection of immunized mice. DoHH2 cell or monkey peripheral blood mononuclear cell suspensions were centrifuged and the cells were resuspended in PBS containing 0.1% BSA and counted. The serum to be tested of each group of immunized mice was added. After 60 min of incubation at room temperature, the cells were washed for three times and then anti-mouse IgG Fc-FITC secondary antibody was added. After 30 min of incubation at room temperature in the dark, the cells were washed for three times and gently resuspended in PBS containing 0.1% BSA for detection on the instrument.

The results of ELISA and FACS serum titer detection for each group of mice are shown in FIG. 1 to FIG. 7.

Figure 2:
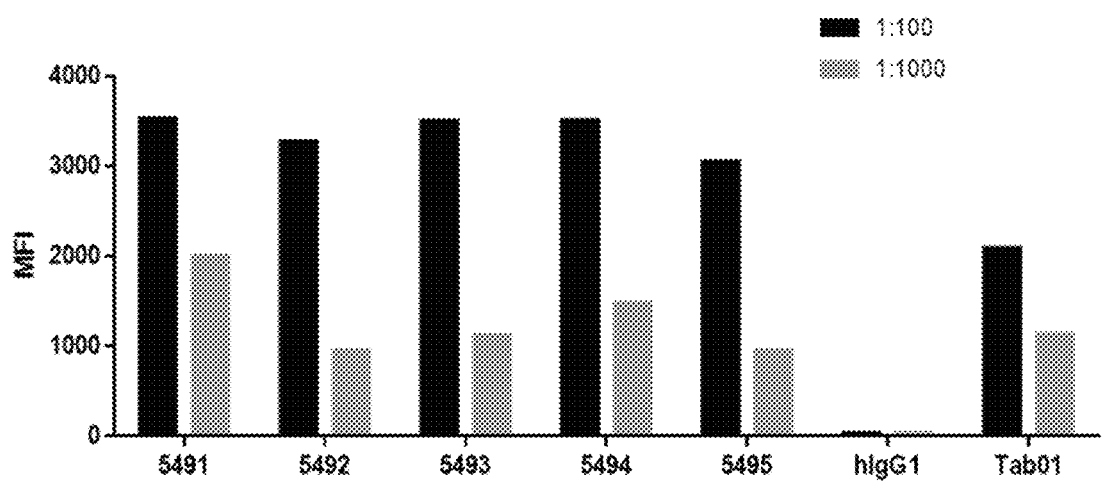
FIG. 2: FACS detection results of serum titer of Balb/c mice immunized with human CD79B ECD-hFc protein.

Five Balb/c mice were immunized with human CD79b ECD-hFc protein, numbered 5491, 5492, 5493, 5494 and 5495. The results of ELISA serum titer detection are shown in FIG. 1. The results showed that the serum titer in immunized mouse reached more than 1:100K. The results of FACS serum detection of mice are shown in FIG. 2. It can be seen that the antibodies produced in mouse serum could specifically recognize the CD79B protein on the surface of DoHH2 cells.

Figure 3:
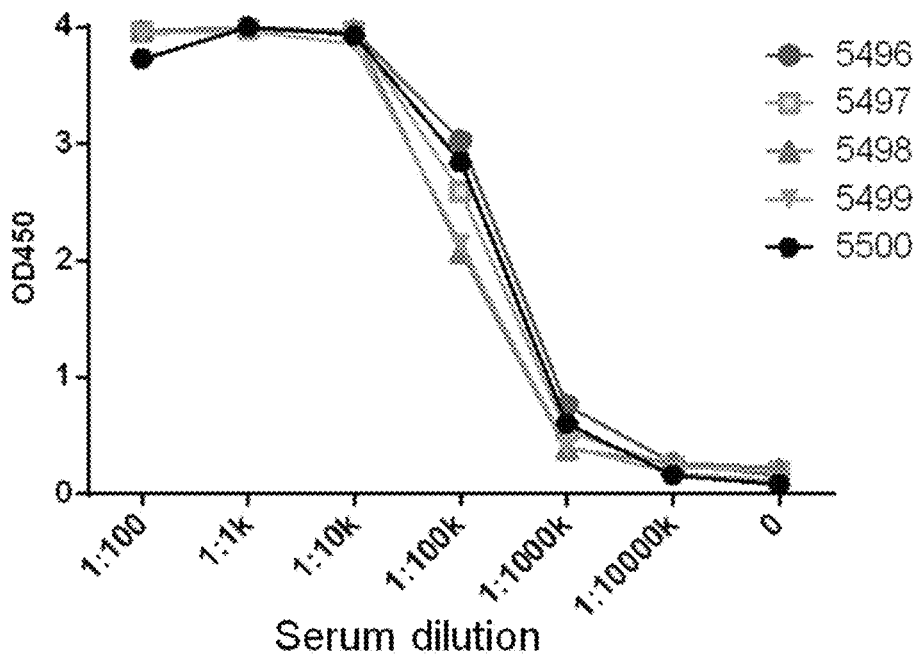
FIG. 3: ELISA detection results of serum titer of SJL mice immunized with human CD79B ECD-hFc protein.
Figure 4:
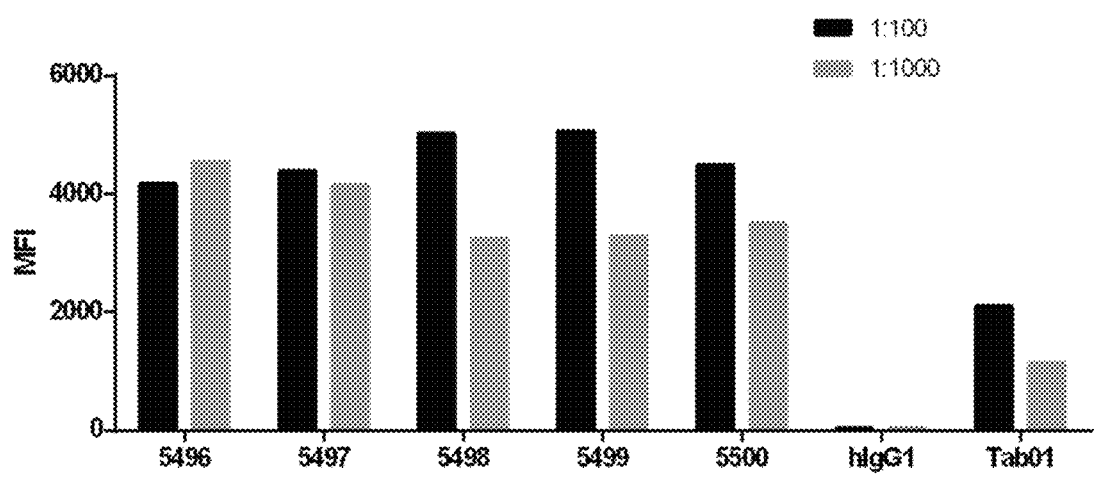
FIG. 4: FACS detection results of serum titer of SJL mice immunized with human CD79B ECD-hFc protein.

Five SJL mice were immunized with human CD79b ECD-hFc protein, numbered 5496, 5497, 5498, 5499 and 5500. The results of ELISA serum titer detection are shown in FIG. 3. The results showed that the serum titer in immunized mouse reached more than 1:100K. The results of FACS serum detection of mice are shown in FIG. 4. It can be seen that the antibodies produced in mouse serum could specifically recognize the CD79B protein on the surface of DoHH2 cells.

Figure 5:
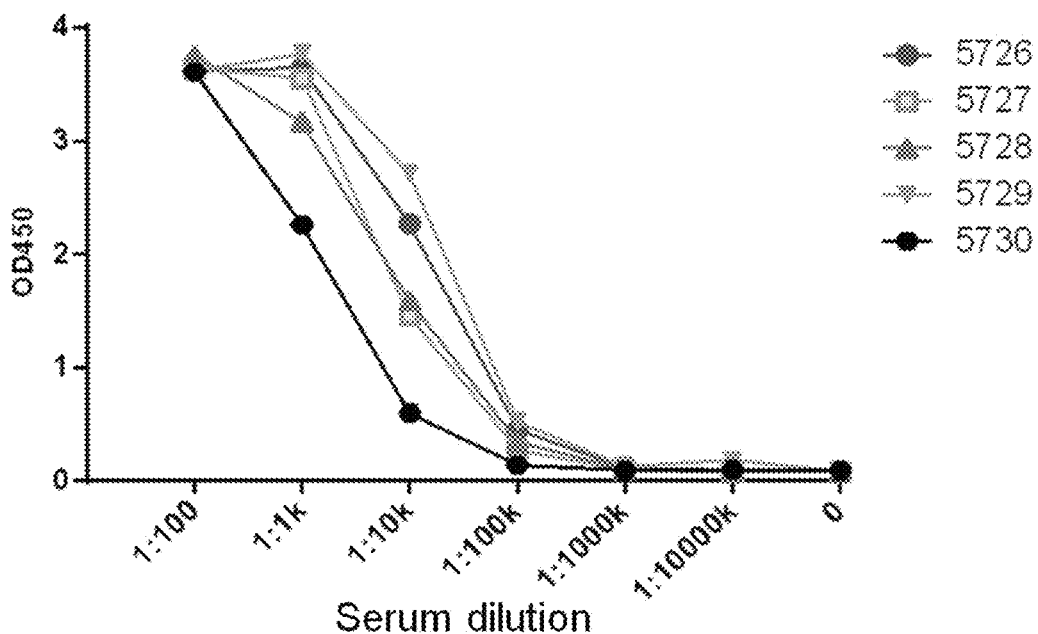
FIG. 5: ELISA detection results of serum titer of SJL mice immunized with human CD79B ECD-his protein.
Figure 6:
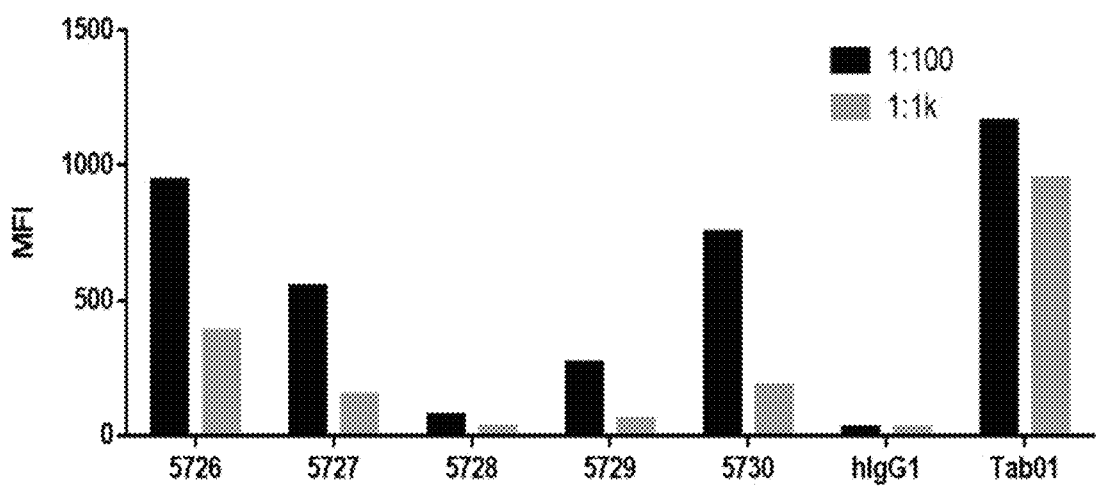
FIG. 6: FACS detection results of serum titer of SJL mice immunized with human CD79B ECD-his protein.
Figure 7:
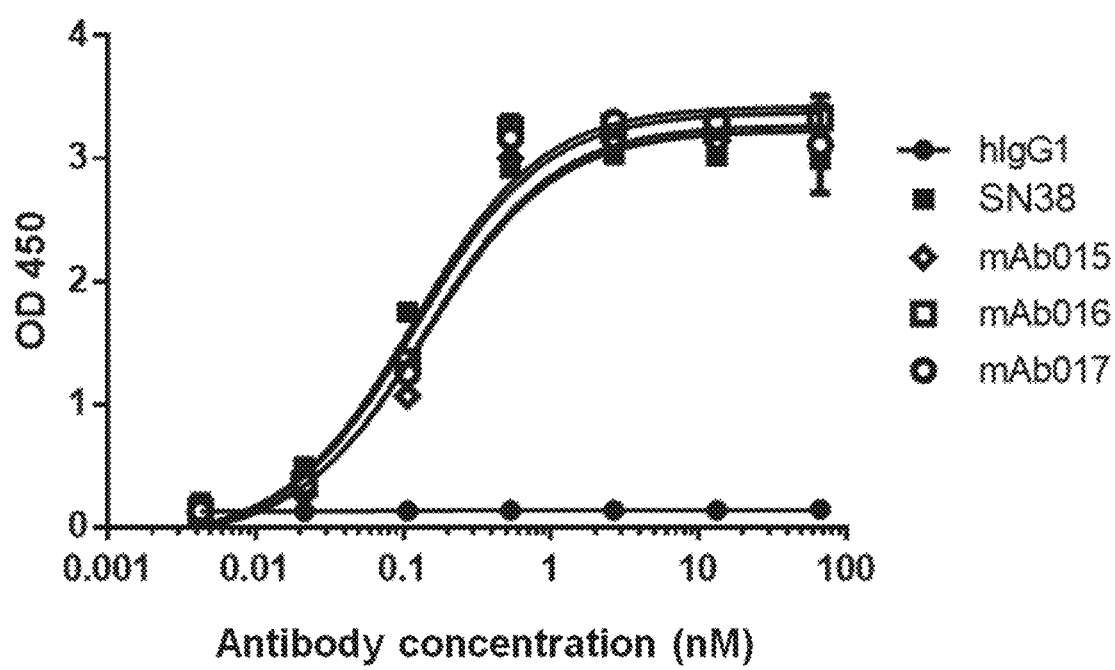
FIG. 7: ELISA detection results of anti-human CD79B murine monoclonal antibodies, wherein hIgG1 is negative control antibody and SN8 is positive control antibody.

Five SJL mice were immunized with human CD79b ECD-his protein, numbered 5726, 5727, 5728, 5729 and 5730. The results of ELISA serum titer detection are shown in FIG. 5. The results showed that the serum titer in immunized mouse reached more than 1:10K. The results of FACS serum detection of mice are shown in FIG. 6. It can be seen that the antibodies produced in mouse serum could specifically recognize the CD79B protein on the surface of DoHH2 cells.

From the above results, it can be known that the immunized mice produced specific antibodies against CD79B, and the above mice could be used for cell fusion to generate hybridoma cell lines capable of secreting specific antibodies against CD79B.

2. Hybridoma Preparation and Antibody Screening

Cell fusion is spontaneous or artificially induced to promote the fusion of mouse lymphocytes and myeloma cells SP2/0 (ATCC, CCL-121™) into hybridoma cells, which have the function of antibody secretion and can proliferate indefinitely. Lymphocytes of the immunized group of mice and myeloma cells were fused by using the electrofusion method, and the hybridoma cells were used for subsequent antibody screening.

1) Electrofusion experiment. One week before fusion, SP2/0 cells were expanded in 10% DMEM medium. The spleen and lymph nodes were removed from the sacrificed mice in a biological safety cabinet, washed and ground in petri dishes, and the lymphocytes were collected. SP2/0 and lymphocytes was mixed in proportion, and fusion was performed with the electrofusion instrument, and the program was set up. After fusion, the cells were plated in a 96-well plate and cultured in a 37° C., 5% $CO_2$ incubator. The cell status was observed every day, and the cell fusion rate was counted 5 days after fusion. The fused hybridoma cells were screened 9-14 days after fusion, and the cells in positive well were selected for expansion in a 24-well plate.

2) Subcloning by limited dilution method. The cell lines to be subcloned were resuspended from the 24-well culture wells and counted. Each cell line was diluted to a cell concentration of 5-10 cells/mL. The diluted cell suspension was added to 15 cm disposable culture dishes and 0.2 mL was added to each well of a 96-well culture plate, with each well containing 1-2 cells. The 96-well plate innoculated with the cells was placed in a 37° C., 5% $CO_2$ incubator for culture. After 7-10 days, the subcloning plate was detected and screened according to the growth status of the cells, and positive clones were selected and transferred into 24 wells for further positive confirmation.

3) ELISA screening. Before the start of the experiment, a 96-well plate was labeled accordingly and coated with an antigen at a concentration of 1 μg/mL, 50 μl per well overnight in a refrigerator at 4° C. The next day, the antigen plate coated the day before was taken out and washed with a plate washer (washing solution: 1×PBST). After washing, the plate was blocked with 1% BSA blocking solution prepared in 1×PBST at 37° C. for 1 h. After washing the plate with 1×PBST washing solution for 3 times, 50 μl of cell supernatant to be tested were added and incubated in a 37° C. incubator for 1 h. After washing the plate with 1×PBST washing solution for 3 times, 100 μl 1:5000 diluted goat-anti-mouse secondary antibody was added and incubated in a 37° C. incubator for 0.5 h. After washing the plate, TMB chromogenic solution A and B were mixed at a 1:1 ratio and then color development was carried out. The development reaction was terminated with 1 N hydrochloric acid after 15 min. The fluorescence values at 450 nm were detected on a Spectra Max M5 multi-function plate reader.

4) FACS screening. DoHH2 cell suspensions were centrifuged and the cells were resuspended in PBS containing 0.1% BSA and counted. The cell supernatant to be tested was added. After 60 min of incubation at room temperature, the cells were washed for three times and then anti-mouse IgG Fc-FITC secondary antibody was added. After 30 min of incubation at room temperature in the dark, the cells were washed for three times and gently resuspended in PBS containing 0.1% BSA for detection on the instrument.

5) Identification of positive hybridoma clones. After fusion and subclone screening of mouse spleen cells, we obtained a number of specific antibodies against human CD79B antigen. Among them, 17 hybridomas with the best ELISA and FACS binding ability were used for antibody production and purification. The ELISA detection results of the culture supernatant of anti-human CD79B hybridoma positive clone cells are shown in Table 1. The FACS detection results of the culture supernatant of anti-human CD79B hybridoma positive clone cells are shown in Table 2. mIgG was used as a negative control in both ELISA and FACS tests.

TABLE 1

ELISA detection results of anti-human CD79B hybridoma positive clones

| Antibody number | Clone number | Detection results(OD450) |
| --- | --- | --- |
| Negative control | mIgG | 0.05 |
| mAb001 | 12A11-1G1 | 3.26 |
| mAb002 | 19F10-1D7 | 3.69 |
| mAb003 | 51E5G6 | 3.02 |
| mAb004 | 67B10C1 | 3.41 |
| mAb005 | 78A9F4 | 3.73 |
| mAb006 | 48F11D6 | 3.34 |
| mAb007 | 61A11F1 | 3.40 |
| mAb008 | 63G2A2 | 3.56 |
| mAb009 | 75F1E2 | 3.57 |
| mAb010 | 66G3E7 | 3.83 |
| mAb011 | 66E12H3 | 3.41 |
| mAb012 | 73A8F3 | 3.45 |
| mAb013 | 74C4F3 | 3.31 |
| mAb014 | 70B8B3 | 3.10 |
| mAb015 | 83B2G2 | 3.41 |
| mAb016 | 83C2D4 | 3.46 |
| mAb017 | 86F11F6 | 3.80 |

TABLE 2

FACS detection results of anti-human CD79B hybridoma positive clones

| Antibody number | Clone number | Mean fluorescence values |
| --- | --- | --- |
| Negative control | mIgG | 58 |
| mAb001 | 12A11-1G1 | 13032 |
| mAb002 | 19F10-1D7 | 5943 |
| mAb003 | 51E5G6 | 33918 |
| mAb004 | 67B10C1 | 26000 |
| mAb005 | 78A9F4 | 24454 |
| mAb006 | 48F11D6 | 20120 |
| mAb007 | 61A11F1 | 18039 |
| mAb008 | 63G2A2 | 16453 |
| mAb009 | 75F1E2 | 16001 |
| mAb010 | 66G3E7 | 15897 |
| mAb011 | 66E12H3 | 14688 |
| mAb012 | 73A8F3 | 14073 |
| mAb013 | 74C4F3 | 12894 |
| mAb014 | 70B8B3 | 8776 |
| mAb015 | 83B2G2 | 10036 |
| mAb016 | 83C2D4 | 9990 |
| mAb017 | 86F11F6 | 8132 |

3. Production, Purification and Identification of Murine Monoclonal Antibodies

1) Production and purification of murine monoclonal antibodies. The hybridoma cells used for antibody production were observed under a microscope. The cells were collected when growing to more than 70% and in good cell condition, and counted with a Countstar IC1000 cell counter. The cell concentration was adjusted to $1 \times 10^5$ to $5 \times 10^5$ cells/mL with a well-prepared medium, and the cells were transferred to Roller Bottles. The Roller Bottles with cells transferred were loaded onto a roller bottle incubator for incubation at 37° C. for 10-15 days. The cell growth status was observed every day. The culture was taken out for purification after the medium turned orange and transparent. The antibodies were purified by passing the cell supernatant through Protein A columns, the purification was operated in accordance with conventional methods.

2) ELISA detection of anti-human CD79B murine monoclonal antibodies. Before the start of the experiment, a 96-well plate was labeled accordingly and coated with an antigen at a concentration of 1 µg/mL, 50 µl per well overnight in a refrigerator at 4° C. The next day, the antigen plate coated the day before was taken out and washed with a plate washer (washing solution: 1×PBST) for once. After washing, the plate was blocked with 1% BSA blocking solution prepared in 1×PBST at 37° C. for 1 h. After washing the plate with 1×PBST washing solution for 3 times, 50 µl of antibody, diluted to 100 nM (by 1:10), were added and incubated in a 37° C. incubator for 1 h. After washing the plate with ×PBST washing solution for 3 times, 100 µl 1:5000 diluted goat-anti-mouse secondary antibody was added and incubated in a 37° C. incubator for 0.5 h. After washing the plate, TMB chromogenic solution A and B were mixed at a 1:1 ratio and then color development was carried out. The development reaction was terminated with 1 N hydrochloric acid after 15 min. The fluorescence values at 450 nm were detected on a Spectra Max M5 multi-function plate reader. Among them, three anti-human CD79B murine monoclonal antibodies had the strongest ELISA binding ability, including mAb015, mAb016 and mAb017 (see FIG. 7 for specific data). Among them, hIgG1 was the negative control antibody and SN8 was the positive control antibody. SN8 is the antibody used in the antibody-conjugated drug polatuzumab vedotin developed by Roche Pharmaceuticals (for the sequence, refer to the source of the sequence: US20170362318A). At present, polatuzumab vedotin has been approved by the FDA for marketing. It can be seen from the results that in the ELISA experiment, the binding ability of the three anti-human CD79B murine monoclonal antibodies mAb015, mAb016 and mAb017 selected preferably by the present disclosure was similar to that of SN8.

Figure 8:
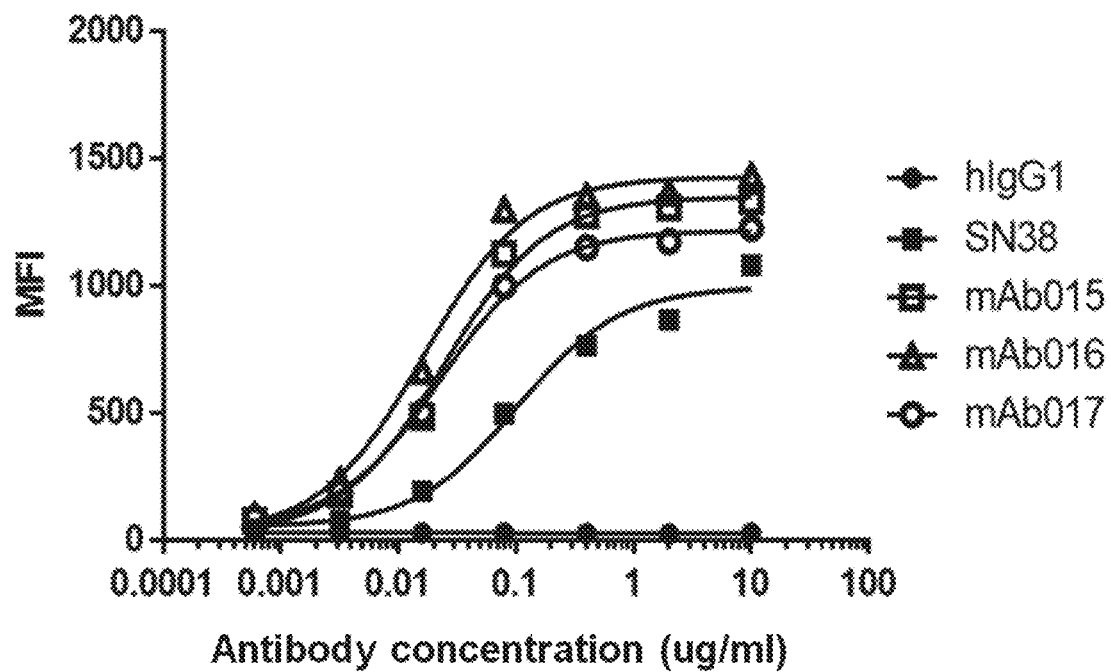
FIG. 8: FACS detection results of anti-human CD79B murine monoclonal antibodies, wherein hIgG1 is negative control antibody and SN8 is positive control antibody.

3) FACS detection of anti-human CD79B murine monoclonal antibodies. After centrifugation of the DOHH2 cell suspension, the cells were resuspended in PBS containing 0.1% BSA and counted. 100 µl of antibody diluted to 100 nM (by 1:10) was added and incubated for 1 h at room temperature. After washing the cells for three times, anti-mouse IgG Fc-FITC secondary antibody was added. After 30 min of incubation at room temperature in the dark, the cells were washed for three times and gently resuspended in PBS containing 0.1% BSA for testing on an instrument. Among them, three anti-human CD79B murine monoclonal antibodies had the strongest FACS binding ability, including mAb015, mAb016 and mAb017 (see FIG. 8 for specific data). Among them, hIgG1 was the negative control antibody and SN8 was the positive control antibody. It can be known from the results that in the FACS experiment, the binding ability of the three anti-human CD79B murine monoclonal antibodies mAb015, mAb016 and mAb017 selected preferably by the present disclosure was better than that of SN8.

Figure 9:
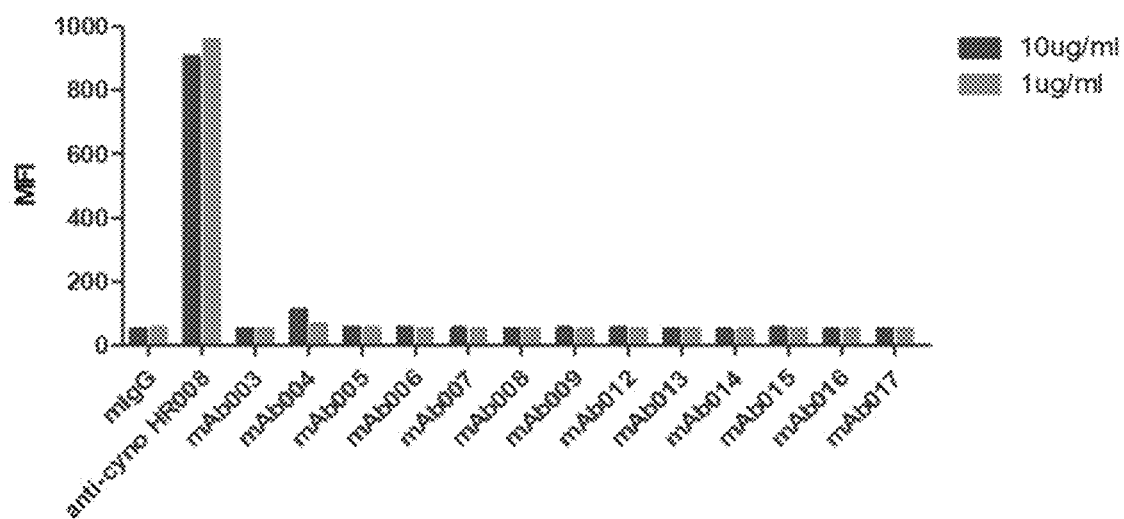
FIG. 9: FACS detection results for the cross-reactivity of anti-human CD79B murine monoclonal antibodies, wherein mIgG is negative control antibody; anti-cyno HR008, an anti-cyno CD79B murine monoclonal antibody, the antibody sequence of which is derived from the anti-cyno CD79B murine monoclonal antibody (clone number 10D10) in patent WO2009012268A1, is positive control antibody.

4) FACS detection of cross-activity of anti-human CD79B murine monoclonal antibodies. 293F-cynoCD79B cells were obtained by transient transfection method. After the cell suspension was centrifuged, the cells were resuspended in PBS containing 0.1% BSA and counted. 100 µl of antibody was added at concentrations of 10 µg/mL and 1 µg/mL, respectively. The cells were incubated for 1 h at room temperature. After washing the cells for three times, anti-mouse IgG Fc-FITC secondary antibody was added. After 30 min of incubation at room temperature in the dark, the cells were washed for three times and gently resuspended in PBS containing 0.1% BSA for detection on an instrument. The results of FACS detection showing the cross-activity of anti-human CD79B murine monoclonal antibodies are shown in FIG. 9, wherein mIgG1 is negative control antibody, anti-cyno HR008 is an anti-cyno CD79B murine monoclonal antibody, the antibody sequence of which is derived from the anti-cyno CD79B murine monoclonal antibody (clone number 10D10) in patent WO2009012268A1. It can be seen from the results that all anti-human CD79B murine monoclonal antibodies screened in this disclosure did not recognize cyno CD79B.

5) SPR detection of anti-human CD79B murine monoclonal antibodies. The affinity between anti-human CD79B antibody and its antigen human CD79B-His was detected by surface plasmon resonance (SPR). The antigen human CD79B-His protein was immobilized to the CM5 chip. The coupling level was set at 100 RU. The running buffer was HBS-EP+(10 mM HEPES, 150 mM NaCl, 3 mM EDTA, 0.05% surfactant P20). The diluted antibody flew through the experimental channel and the control channel at a flow rate of 30 μl/min for 3 min, and the dissociation was performed for 5 min. Then the regenerate buffer (10 mM glycine buffer, pH 1.5) was run at a flow rate of 30 μl/min for 30 sec. The data was analyzed with Biacore 8K evaluation software.

Example 3. Determination of the Amino Acid Sequence of the Murine Monoclonal Antibody Variable Region The high-affinity hybridoma monoclonal cell lines obtained in Example 2 were subjected to amino acid sequence determination of the variable region. Then human and mouse chimeric antibodies (cAb) were recombinantly expressed, and then further antibody identification was performed. The heavy and light chain variable regions of the antibody gene were amplified by reverse transcription PCR, linked to a vector and sequenced to obtain the light and heavy chain sequence of the monoclonal antibody. First, total cellular RNA of the single cell lines with good activity in Example 2 was extracted by using RNA purification kit (Qiagen, article number 74134, see the specification for the steps). Then the single-stranded cDNA was prepared by using cDNA synthesis kit (Invitrogen, article number 18080-051), that is, Oligo-dT primer cDNA reverse transcription. It was used as a template to synthesize the antibody light and heavy chain variable region sequences by using PCR method, and the PCR product was cloned into the TA vector pMD-18T and then sent for sequencing. The obtained antibody light and heavy chain sequences were respectively cloned into an expression vector (see Example 1 for the method), the recombinant monoclonal antibody was expressed, and the activity was verified (see Example 2 for the method), and then the humanization work was carried out.

The amino acid residues of the VH/VL CDR of the anti-human CD79B antibody in the present disclosure are determined and annotated by the Chothia numbering system.

>The heavy chain variable region of murine hybridoma monoclonal antibody mAb015:
(SEQ ID NO: 3)
QVQLQQSGAELARPGASVKLSCKASGSSFTSYGINWVKQRTGQGLEWIGEI

FPRSGNTYYNEKFEGKATLTADKSSSTAYMELRSLTSEDSAVYFCAKGDLG

DFDYWGQGTTLTVSS.

>The light chain variable region of murine hybridoma monoclonal antibody mAb015:
(SEQ ID NO: 4)
DFLMTQTPLSLPVRLGDQASISCRSSQSIVHSDGNTYFEWYLQKPGQSPKL

LIYKVSNRFSGVPDRFSGSGSGTDFTLKISRVEAEDLGVYYCFQGSHVPWT

FGGGTKLEIK.

>The heavy chain variable region of murine hybridoma monoclonal antibody mAb017:
(SEQ ID NO: 5)
QVQLQQSGAELARPGASVKLSCKASGYTFTTYGINWVKQRTGQGLEWIGEI

YPRSGNIYYNEKFKGKATLTADKSSSTAYMELRSLTSEDSAVYFCARGSDY

DGDFAYWGQGTLVTVSA.

>The light chain variable region of murine hybridoma monoclonal antibody mAb017:
(SEQ ID NO: 6)
DVLMTQTPLSLPVSLGDQASISCRSSQSIVHHDGNTYLEWYLQKPGQSPKL

LIYKVSNRFSGVPDRFSGSGSGTDFTLKISRVEAEDLGVYYCFQGSHVPWT

FGGGTQLEIK.

>The heavy chain variable region of murine hybridoma monoclonal antibody mAb016:
(SEQ ID NO: 17)
QVQLQQSGAELARPGASVKLSCKASGYIFTNYGIIWVKQRTGQGLEWIGDI

FPGSGNTYYNENFKGKATLTADKSSSTAYMELRSLTSEDSAVYFCSRGELG

DFDYWGQGTTLTVSS.

>The light chain variable region of murine hybridoma monoclonal antibody mAb016:
(SEQ ID NO: 18)
VVLMTQTPLSLPVSLGDQASISCRSSQNIVHSDGTTYLEWYLQKPGQSPKL

LIYKVSNRFSGVPDRFSGSGSGTDFTLKISRVEAEDLGIYYCFQGSHVPWT

FGGGTKLEIK.

The murine CDR sequences according to the Chothia numbering rules are shown in Table 3:

TABLE 3

| CDR sequences of murine anti-human CD79B antibodies | | | |
|---|---|---|---|
| CDR | mAb015 | mAb016 | mAb017 |
| Heavy chain CDR1 | GSSFTSY (SEQ ID NO: 7) | GYIFTNY (SEQ ID NO: 23) | GYTFTTY (SEQ ID NO: 13) |
| Heavy chain CDR2 | FPRSGN (SEQ ID NO: 8) | FPGSGN (SEQ ID NO: 24) | YPRSGN (SEQ ID NO: 14) |

TABLE 3-continued

CDR sequences of murine anti-human CD79B antibodies

| CDR | mAb015 | mAb016 | mAb017 |
|---|---|---|---|
| Heavy chain CDR3 | GDLGDFDY (SEQ ID NO: 9) | GELGDFDY (SEQ ID NO: 25) | GSDYDGDFAY (SEQ ID NO: 15) |
| Light chain CDR1 | RSSQSIVHSDGNTYFE (SEQ ID NO: 10) | RSSQNIVHSDGTTYLE (SEQ ID NO: 26) | RSSQSIVHHDGNTYLE (SEQ ID NO: 16) |
| Light chain CDR2 | | KVSNRFS (SEQ ID NO: 11) | |
| Light chain CDR3 | | FQGSHVPWT (SEQ ID NO: 12) | |

Example 4. Humanization of Anti-Human CD79B Antibodies

After aligning the homology of the light and heavy chain sequences of the murine anti-CD79B monoclonal antibodies obtained in Example 3 against the antibody database, a humanized antibody model was established. According to the model, the optimal humanized anti-CD79B monoclonal antibodies were selected as preferred molecules by back mutation screening. This method started from searching the published murine Fab crystal structure model database (such as PDB database) for crystal structures similar or homologous to that of the obtained murine candidate molecules, and the Fab crystal structures with high resolution (such as <2.5 Å) were selected for the establishment of a mouse Fab model. The mouse antibody light and heavy chain sequences were compared with the sequences in the model. The sequences consistent with the murine antibody sequences in the model were retained to obtain the structure model of the murine antibody; the inconsistent amino acids were the potential back mutation sites. The murine antibody structure model was run with Swiss-pdb viewer software to optimize the energy (minimization). The different amino acid positions in the model (except CDRs) were subjected to back-mutation, and the obtained (humanized) mutant antibodies were compared with the antibodies before humanization for activity detection. Humanized antibodies with good activity were retained. Afterwards, the CDR regions were optimized, including avoiding glycosylation, deamidation and oxidation sites. The antibodies described above were cloned, expressed, and purified by gene cloning and recombinant expression methods. After detection by SPR, etc., the humanized antibodies hAb015 and hAb017 which retained the best activity were finally selected. See Table 4 for specific data. Humanized antibodies hAb015 and hAb017 maintained similar affinity and related functions as the murine monoclonal antibodies.

TABLE 4

Identification results of humanized anti-CD79B antibodies

| Detection method | Protein/cell line | SN8 | hAb015 | hAb017 |
|---|---|---|---|---|
| SPR detection (Kd, nM) | Human CD79B-His protein | 5.98 | 0.43 | 3.77 |
| Cell killing experiment (IC$_{50}$, ng/ml) | DoHH2 cells | 4229.0 | 473.5 | / |
| | Raji cells | >10000 | >10000 | / |
| Interspecies cross-reactivity | Human CD79B-His protein | Yes | Yes | Yes |
| | Cyno CD79B-His protein | No | No | No |
| | Murine CD79B-His protein | No | No | No |
| Thermal stability detection | DSC (Tm, ° C.) | 63 | 60 | 65 |
| | DLS (Tagg, ° C.) | 61 | 62 | 67 |

Note:
(/ means no detection waas carried out)

The sequences of humanized antibodies hAb015 and hAb017 are shown below.

>The heavy chain sequence of the humanized antibody hAb015:
(SEQ ID NO: 19)
EVQLVQSGAEVKKPGSSVKVSCKASGSSFSSYGINWVKQAPGQGLEWIGEI

FPRSGNTYYNEKFEGRATLTADKSTSTAYMELRSLRSEDTAVYYCAKGDLG

DFDYWGQGTTVTVSSASTKGPSVFPLAPSSKSTSGGTAALGCLVKDYFPEP

VTVSWNSGALTSGVHTFPAVLQSSGLYSLSSVVTVPSSSLGTQTYICNVNH

KPSNTKVDKKVEPKSCDKTHTCPPCPAPELLGGPSVFLFPPKPKDTLMISR

TPEVTCVVVDVSHEDPEVKFNWYVDGVEVHNAKTKPREEQYNSTYRVVSVL

TVLHQDWLNGKEYKCKVSNKALPAPIEKTISKAKGQPREPQVYTLPPSREE

MTKNQVSLTCLVKGFYPSDIAVEWESNGQPENNYKTTPPVLDSDGSFFLYS

KLTVDKSRWQQGNVFSCSVMHEALHNHYTQKSLSLSPGK.

>The light chain sequence of the humanized antibody hAb015:
(SEQ ID NO: 20)
DFVMTQTPLSLPVTPGEPASISCRSSQSIVHSDGNTYFEWYLQKPGQSPKL

LIYKVSNRFSGVPDRFSGSGSGTDFTLKISRVEAEDVGVYYCFQGSHVPWT

FGGGTKVEIKRTVAAPSVFIFPPSDEQLKSGTASVVCLLNNFYPREAKVQW

KVDNALQSGNSQESVTEQDSKDSTYSLSSTLTLSKADYEKHKVYACEVTHQ

GLSSPVTKSFNRGEC.

-continued

>The heavy chain sequence of the humanized
antibody hAb017:
(SEQ ID NO: 21)
EVQLVQSGAEVKKPGASVKVSCKASGYTFTTYGINWVKQAPGQGLEWIGEI

YPRSGNIYYNEKFKGKATLTADKSTSTAYMELRSLRSDDTAVYYCARGSDY

DGDFAYWGQGTLVTVSSASTKGPSVFPLAPSSKSTSGGTAALGCLVKDYFP

EPVTVSWNSGALTSGVHTFPAVLQSSGLYSLSSVVTVPSSSLGTQTYICNV

NHKPSNTKVDKKVEPKSCDKTHTCPPCPAPELLGGPSVFLFPPKPKDTLMI

SRTPEVTCVVVDVSHEDPEVKFNWYVDGVEVHNAKTKPREEQYNSTYRVVS

VLTVLHQDWLNGKEYKCKVSNKALPAPIEKTISKAKGQPREPQVYTLPPSR

EEMTKNQVSLTCLVKGFYPSDIAVEWESNGQPENNYKTTPPVLDSDGSFFL

YSKLTVDKSRWQQGNVFSCSVMHEALHNHYTQKSLSLSPGK.

>The light chain sequence of the humanized
antibody hAb017:
(SEQ ID NO: 22)
DVVMTQTPLSLPVTPGEPASISCRSSQSIVHHDGNTYLEWYLQKPGQSPQL

LIYKVSNRFSGVPDRFSGSGSGTDFTLKISRVEAEDVGVYYCFQGSHVPWT

FGGGTKVEIKRTVAAPSVFIFPPSDEQLKSGTASVVCLLNNFYPREAKVQW

KVDNALQSGNSQESVTEQDSKDSTYSLSSTLTLSKADYEKHKVYACEVTHQ

GLSSPVTKSFNRGEC.

Example 5. Endocytosis of Anti-CD79B Antibodies

In order to test whether the CD79B antibodies in the present disclosure could be endocytosed into cells together with human CD79B after binding to human CD79B, an endocytosis experiment was performed with DOHH-2 cells (DSMZ, ACC 47) with high expression level of human CD79B protein to evaluate the capacity of the antibodies to be endocytosed.

DOHH-2 cells were cultured according to the conventional method suitable for suspension cells. The composition of the complete medium was: RPMI 1640 medium (GIBCO, Cat No.: 11835-030), plus 10% (v/v) fetal bovine serum (FBS) (GIBCO, Cat No.: 10099-141) and penicillin/streptomycin (GIBCO, Cat No.: 15070-063).

In the experiment, the cells were collected by low-temperature centrifugation at 4° C., 1000 rpm for 5 min. The cells were resuspended in 10-15 ml of FACS buffer pre-cooled on ice. The composition of the FACS buffer was: phosphate buffered saline (PBS), pH 7.4, plus 2% fetal bovine serum (FBS). During the entire experiment, the FACS buffer was pre-cooled on ice. After centrifugation and counting, the cells were added to a 96-well plate at 300,000 cells/well. After centrifugation and discarding the supernatant, 12.5 g/ml Fc blocking solution (BD, Cat No.: 564220) was added at 100 μl/well. The cells were blocked at room temperature for 10 min. Then 20 μg/ml of the CD79B antibodies to be tested were added to the corresponding wells and incubated at 4° C. in the dark for 1 h. The cells were washed twice with pre-cooled PBS buffer to remove unbound antibodies. Cell complete medium (RPMI 1640 medium with 10% fetal bovine serum) was added and the cells were incubated at 37° C. and 5% $CO_2$ for 0 h, 1 h, 2 h or 4 h. After centrifugation and discarding the supernatant, 100 μl/well of 2% PFA buffer was added. The cells were resuspended and let stand for 10 min. Then the cells were washed with FACS buffer for 3 times, then 100 μl of secondary antibody solution (fluorescence-labeled goat-anti-human secondary antibody: 1:250 dilution with a concentration of 2 μg/ml, Biolegend, Cat #409304) was added and incubate at 4° C. in the dark for 0.5 h. Pre-cooled PBS buffer was added and centrifuged at 4° C. to discard the supernatant, repeating for three times. The cells were resuspended in FACS buffer at 200 μl/well and detected by flow cytometry (BD FACS Calibur).

The results showed that none of the three antibodies, SN8, hAb015 and hAb017, could be endocytosed by DOHH-2 cells when incubated at 4° C. Meanwhile, when incubated at 37° C., most of the antibodies had been endocytosed by DOHH-2 cells after 1 h, and the antibody endocytosis reached the maximum after 4 h. All 3 antibodies were relatively well endocytosed.

What claimed is:

1. An anti-human CD79B antibody or antigen-binding fragment thereof, which comprises any one selected from of the following (I) to (II):

(1) a heavy chain variable region, comprising HCDR1, HCDR2 and HCDR3 as shown in SEQ ID NO: 7 or SEQ ID NO: 27, SEQ ID NO: 8, and SEQ ID NO: 9, respectively; and a light chain variable region, comprising LCDR1, LCDR2 and LCDR3 as shown in SEQ ID NO: 10, SEQ ID NO: 11 and SEQ ID NO: 12, respectively; (II) a heavy chain variable region, comprising HCDR1, HCDR2 and HCDR3 as shown in SEQ ID NO: 13, SEQ ID NO: 14 and SEQ ID NO: 15, respectively; and a light chain variable region, comprising LCDR1, LCDR2 and LCDR3 as shown in SEQ ID NO: 16, SEQ ID NO: 11 and SEQ ID NO: 12, respectively.

2. The anti-human CD79B antibody or antigen-binding fragment thereof according to claim 1, wherein:

(I) the heavy chain variable region comprises the sequence as shown in SEQ ID NO: 3 or the sequence with at least 90%, 95%, 98%, 99% identity with SEQ ID NO: 3; and the light chain variable region comprises: the sequence as shown in SEQ ID NO: 4 or the sequence with at least 90%, 95%, 98%, 99% identity with SEQ ID NO: 4;

(II) the heavy chain variable region comprises the sequence as shown in SEQ ID NO: 5 or the sequence with at least 90%, 95%, 98%, 99% identity with SEQ ID NO: 5; and the light chain variable region comprises: the sequence as shown in SEQ ID NO: 6 or the sequence with at least 90%, 95%, 98%, 99% identity with SEQ ID NO: 6.

3. The anti-human CD79B antibody or antigen-binding fragment thereof according to claim 1, which is a murine antibody, a chimeric antibody, or a humanized antibody or fragment thereof.

4. The anti-human CD79B antibody or antigen-binding fragment thereof according to claim 3, wherein:

the heavy chain variable region of the humanized antibody comprises the heavy chain framework region of human IgG1, IgG2, IgG3 or IgG4 or variant thereof; and the antigen-binding fragment is selected from the group consisting of Fab, Fab'-SH, Fv, scFv and/or (Fab')$_2$ fragment.

5. An antibody-drug conjugate, wherein the antibody comprises the anti-human CD79B antibody or antigen-binding fragment thereof according to claim 1 wherein the antibody-drug conjugate comprises a cytotoxic agent.

6. A polynucleotide encoding the anti-human CD79B antibody or antigen-binding fragment, wherein:
the anti-human CD79B antibody or antigen-binding fragment thereof, which comprises any one selected from of the following (I) to (II):
(I) a heavy chain variable region, comprising HCDR1, HCDR2 and HCDR3 as shown in SEQ ID NO: 7, SEQ ID NO: 8 and SEQ ID NO: 9, respectively; and
a light chain variable region, comprising LCDR1, LCDR2 and LCDR3 as shown in SEQ ID NO: 10, SEQ ID NO: 11 and SEQ ID NO: 12, respectively;
(II) a heavy chain variable region, comprising HCDR1, HCDR2 and HCDR3 as shown in SEQ ID NO: 13, SEQ ID NO: 14 and SEQ ID NO: 15, respectively; and
a light chain variable region, comprising LCDR1, LCDR2 and LCDR3 as shown in SEQ ID NO: 16, SEQ ID NO: 11 and SEQ ID NO: 12, respectively.

7. A vector comprising the polynucleotide according to claim 6, which is a eukaryotic expression vector, a prokaryotic expression vector or a viral vector.

8. A host cell comprising the vector according to claim 7, wherein the host cell is a bacterial, yeast, or mammalian cell.

9. A method for preparing the anti-human CD79B antibody or antigen-binding fragment thereof, comprising:
expressing the anti-human CD79B antibody or antigen-binding fragment thereof in the host cell according to claim 8, and isolating the anti-human CD79B antibody or antigen-binding fragment thereof from the culture.

10. A pharmaceutical composition, comprising:
any one of or any combination thereof selected from the following: the anti-CD79B antibody or antigen-binding fragment thereof according to claim 1; and,
a pharmaceutically acceptable excipient, diluent or carrier.

11. A method for treating B-cell lymphoma or a B-cell leukemia, the method comprising:
administering to a subject a therapeutically effective amount or disease-delaying effective amount of the anti-human CD79B antibody or antigen-binding fragment thereof according to claim 1,
wherein the B-cell lymphoma is selected from the group consisting of: diffuse large B-cell lymphoma, non-Hodgkin's lymphoma, small lymphocytic lymphoma and mantle cell lymphoma;
wherein the non-Hodgkin's lymphoma is selected from the group consisting of: aggressive NHL, recurrent aggressive NHL, recurrent painless NHL, refractory NHL and refractory painless NHL;
wherein the B-cell leukemia is selected from the group consisting of: chronic lymphocytic leukemia, hairy cell leukemia and acute lymphocytic leukemia.

12. An anti-human CD79B antibody or antigen-binding fragment thereof, which comprises a heavy chain variable region and a light chain variable region, wherein the heavy chain variable region comprises HCDR1, HCDR2 and HCDR3, and the light chain variable region comprises LCDR1, LCDR2 and LCDR3;
wherein the HCDR1, HCDR2, and HCDR3 are identical to complementarity determining regions of the sequence as shown in SEQ ID NO: 19 and the LCDR1, LCDR2, and LCDR3 are identical to complementarity determining regions of the sequence as shown in SEQ ID NO: 20; or
the HCDR1, HCDR2, and HCDR3 are identical to complementarity determining regions of the sequence as shown in SEQ ID NO: 21 and the LCDR1, LCDR2, and LCDR3 are identical to complementarity determining regions of the sequence as shown in SEQ ID NO: 22;
wherein the above CDRs are defined according to the Chothia numbering system.

13. The anti-human CD79B antibody or antigen-binding fragment thereof according to claim 12, wherein:
the heavy chain variable region is identical to the heavy chain variable region of the sequence as shown in SEQ ID NO: 19 or with at least 90%, 95%, 98%, 99% identity with the heavy chain variable region of the sequence as shown in SEQ ID NO: 19; and
the light chain variable region is identical to the light chain variable region of the sequence as shown in SEQ ID NO: 20 or with at least 90%, 95%, 98%, 99% identity with the light chain variable region of the sequence as shown in SEQ ID NO: 20; or
the heavy chain variable region is identical to the heavy chain variable region of the sequence as shown in SEQ ID NO: 21 or with at least 90%, 95%, 98%, 99% identity with the heavy chain variable region of the sequence as shown in SEQ ID NO: 21; and
the light chain variable region is identical to the light chain variable region of the sequence as shown in SEQ ID NO: 22 or with at least 90%, 95%, 98%, 99% identity with the light chain variable region of the sequence as shown in SEQ ID NO: 22.

14. The anti-human CD79B antibody or antigen-binding fragment thereof according to claim 12, which comprises a heavy chain and a light chain, wherein the heavy chain comprising: the sequence as shown in SEQ ID NO: 19 or the sequence with at least 90%, 95%, 98%, or 99% identity with SEQ ID NO: 19; and the light chain comprising: the sequence as shown in SEQ ID NO: 20 or the sequence with at least 90%, 95%, 98%, or 99% identity with SEQ ID NO: 20; or
the heavy chain comprising: the sequence as shown in SEQ ID NO: 21 or the sequence with at least 90%, 95%, 98%, or 99% identity with SEQ ID NO: 21; and
the light chain comprising: the sequence as shown in SEQ ID NO: 22 or the sequence with at least 90%, 95%, 98%, or 99% identity with SEQ ID NO: 22.

15. The anti-human CD79B antibody or antigen-binding fragment thereof according to claim 12, wherein:
the heavy chain variable region of the anti-human CD79B antibody comprises the heavy chain framework region of human IgG1, IgG2, IgG3 or IgG4 or variant thereof;
the antigen-binding fragment is selected from the group consisting of Fab, Fab'-SH, Fv, scFv and/or (Fab')$_2$ fragment.

16. An antibody-drug conjugate, wherein the antibody comprises the anti-human CD79B antibody or antigen-binding fragment thereof according to claim 12,
wherein the antibody-drug conjugate comprises a cytotoxic agent.

17. A polynucleotide encoding the anti-human CD79B antibody or antigen-binding fragment thereof according to claim 12.

18. A vector comprising the polynucleotide according to claim 17, which is a eukaryotic expression vector, a prokaryotic expression vector or a viral vector.

19. A host cell comprising the vector according to claim 18.

20. A method for preparing the anti-human CD79B antibody or antigen-binding fragment thereof, comprising:
    expressing the anti-human CD79B antibody or antigen-binding fragment thereof in the host cell according to claim 19, and isolating the anti-human CD79B antibody or antigen-binding fragment thereof from the culture.

21. A pharmaceutical composition, comprising:
    any one of or any combination thereof selected from the following: the anti-CD79B antibody or antigen-binding fragment thereof according to claim 12; and a pharmaceutically acceptable excipient, diluent or carrier.

22. A method for treating a B-cell lymphoma or a B-cell leukemia, the method comprising:
    administering to a subject a therapeutically effective amount or disease-delaying effective amount of the anti-human CD79B antibody or antigen-binding fragment thereof according to claim 12,
    wherein the B-cell lymphoma is selected from the group consisting of: diffuse large B-cell lymphoma, non-Hodgkin's lymphoma, small lymphocytic lymphoma and mantle cell lymphoma;
    wherein the non-Hodgkin's lymphoma is selected from the group consisting of: aggressive NHL, recurrent aggressive NHL, recurrent painless NHL, refractory NHL and refractory painless NHL;
    wherein the B-cell leukemia is selected from the group consisting of: chronic lymphocytic leukemia, hairy cell leukemia and acute lymphocytic leukemia.

* * * * *